United States Patent
Althumairi et al.

(10) Patent No.: US 11,545,261 B2
(45) Date of Patent: Jan. 3, 2023

(54) HOSPITAL HEALTHCARE PROVIDER MONITORING AND VERIFYING DEVICE AND SYSTEM FOR PATIENT CARE CONDITION

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Azah Althumairi, Riyadh (SA); Joud Abduljawad, Riyadh (SA); Susanna Ferreira, Riyadh (SA); Bandar Alknawy, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 0 days.

(21) Appl. No.: 17/702,853

(22) Filed: Mar. 24, 2022

(65) Prior Publication Data
US 2022/0215940 A1 Jul. 7, 2022

Related U.S. Application Data

(63) Continuation of application No. 17/495,469, filed on Oct. 6, 2021, now Pat. No. 11,322,251.
(Continued)

(51) Int. Cl.
G16H 40/20 (2018.01)
G16H 10/60 (2018.01)
(Continued)

(52) U.S. Cl.
CPC ......... *G16H 40/20* (2018.01); *G06K 19/0723* (2013.01); *G06K 19/0772* (2013.01); *G16H 10/60* (2018.01); *G16H 50/30* (2018.01)

(58) Field of Classification Search
CPC ........ G16H 40/20; G16H 10/60; G16H 50/30; G16H 10/65; G06K 19/0723; G06K 19/0772
(Continued)

(56) References Cited

U.S. PATENT DOCUMENTS 11,211,155 B2   12/2021  Walker
2014/0214441 A1  7/2014  Young et al.
(Continued)

FOREIGN PATENT DOCUMENTS

DE   202020000271 U1   2/2022

*Primary Examiner* — Edwyn Labaze
(74) *Attorney, Agent, or Firm* — Oblon, McClelland, Maier & Neustadt, L.L.P.

(57) ABSTRACT

A hybrid ID system for a medical practitioner and patient care includes a hybrid electronic ID/key having a transmitter device having circuitry for storing ID data and transmitting a signal containing the ID data, and a key having a predetermined shape on a surface of the hybrid electronic ID/key. A radio frequency receptor device having circuitry, storing location information, that detects the signal containing ID data, a matching detection section configured to match the predetermined shape of the key, and a movement tracking portion that tracks movement of the predetermined shape as the key is rotated. A computer system including a patient database is configured to receive the ID data in conjunction with the location information from the radio frequency receptor device when the predetermined shape is completely rotated to a final position, and store the ID data, location information, together with patient data associated with the location.

9 Claims, 45 Drawing Sheets

Related U.S. Application Data

(60) Provisional application No. 63/088,758, filed on Oct. 7, 2020.

(51) Int. Cl.
*G16H 50/30* (2018.01)
*G06K 19/077* (2006.01)
*G06K 19/07* (2006.01)

(58) Field of Classification Search
USPC ............................... 705/2, 1.1; 235/375, 487
See application file for complete search history.

(56) References Cited

U.S. PATENT DOCUMENTS

| | | |
|---|---|---|
| 2014/0379363 A1 | 12/2014 | Hart et al. |
| 2015/0213224 A1 | 7/2015 | Amarasingham et al. |
| 2016/0078180 A1 | 3/2016 | Stackpole |
| 2019/0336085 A1 | 11/2019 | Kayser et al. | iCARE COMMUNICATION PROTOCOL

- iCARE Escalation should be communicated as indicated below
- To ensure streamline process of inpatient's care coordination, all mentioned disciplines are required to adhere to the communication protocol
- BESTCare will support data capturing documentation on the iCARE at Risk Form for auditing purposes

| 602 | 604 | 606 | 608 | 610 | 612 | 614 |
|---|---|---|---|---|---|---|
| Primary Nurse — Primary Nurse will communicate with the charge nurse via iCARE Form in BESTCare | Charge Nurse — Charge Nurse will communicate with the MRP via iCARE Form in BESTCare, and escalate through MS Teams Unit Account, and Paper | MRP — MRP will communicate with the Charge Nurse via iCARE Form in BESTCare, MS Teams Unit Account, and verbally via phone or in-person visit to the ward (as appropriate) | Charge Nurse — Charge Nurse will communicate and escalate to the Head of Division/Chairman via MS Teams Unit Account, and Pager | Charge Nurse — Charge Nurse will communicate and escalate to the CCPID via MS Teams Unit Account, iCARE Email and Regional iCARE Hotline | CCPID — CCPID will communicate with Head of Divisions/Chairmen, Regional Medical Services via MS Teams, iCARE Email, and Pager/Phone | CCPID — CCPID will communicate with the Charge Nurse via MS Teams, iCARE Email, and Pager/Phone |

*CCPID: Corporate Clinical Performance and Innovation Department

STEP 3: Complete the HEALTHCARE PROVIDER Section
- This section is mostly automated but make sure all fields are completed.

HEALTHCARE PROVIDER: — 1602

Nurse Name: Ferreira, Susanna Elizabeth — 1604

Badge No.: 51659 — 1606

Ward/Unit: Corporate Clinical Performance & Innovation Department — 1608

FIG. 16

STEP 4: Complete the PATIENT INFORMATION Section
- This section is also mostly automated but make sure all fields are completed, especially:
  * Diagnosis and
  * MRP

1302

1304 — Patient Name
1306 — Patient MRN
1308 — Patient Unit

- Patient Name:
  Automated function
- Patient MRN:
  Automated function
- Patient Unit:
  Automated function 1710  1712

- Diagnosis:
  Click on search and it will populate the patient's primary diagnosis.
  *If Diagnosis' field remains empty please gently remind MRP to update the patient's diagnosis.
- MRP: Click on search and select the Patient's MRP by Name, BN or Department

1720

1730

Double click on the correct MRP
By default, the selected MRP's information will populate to the correct field within the Patient Information section

STEP 5: Proceed downwards to answer all 9 iCARE Risk Questions as itemized in the Criteria List

| Criteria List | Please indicate with Yes/No | |
|---|---|---|
| 1. Patient is at risk of poorly coordinated care and MRP/their teams are unable to resolve the issue. | ○ Yes | ● No |
| 2. Patient was not physically reviewed by the MRPs since 7 AM the day before. | ○ Yes | ● No |
| 3. Has the Patient/Family raised concerns about the coordination of the patient's care? | ○ Yes | ● No |
| 4. Patient is NOT in the appropriate department or under the appropriate MRP for their current clinical needs. | ○ Yes | ● No |
| 5. Patient require one or more Consultations. | ○ Yes | ● No |
| 6. The Patient was not physically reviewed by the Consultation Service/Team for more than 24 hours from the time of the routine consultation request documented in BESTCARE. | ○ Yes | ● No / NA |
| 7. The Patient was not physically seen by the Consultant of the Consultation Service within 24 hours of a Consultant-to-Consultant communication. | ○ Yes | ● No / NA |
| 8. The Patient was not physically followed up for more than 48 hours by the Consultation Service/Team (when concurrent care required). | ○ Yes | ● No / NA |
| 9. Has the Patient had their Procedure/Images/Echo/Surgery/ Chemotherapy cancelled or delayed (due to non-clinical reasons) as per HARECC rules? | ○ Yes | ● No / NA |

Total iCARE Score: 0

STEP 6: Automated Score

Should none of the items listed on the Criteria List be applicable for your patient an automated score of ZERO will be generated hence no escalation needed.

Very important:

Please remember to save your actions once completed with answering all 9 items as listed on the iCARE Criteria List

Clear Guidelines on iCARE COMMUNICATION PROTOCOL

Take Note:
Any unresolved iCARE issues should be communicated via MS Teams and Email notification. Emails should have the following structure.

TO: Head of Division & Involved MRP

CC: Department Chairman, iCARE Champion, Unit NM, Unit CRN & Your Regional iCARE Support email address (see below)

| iCARE Support email address of your selected region | |
|---|---|
| iCARE KFH-CR | CAREKFHCR@ngha.med.sa |
| iCARE KASCH-CR | CAREKASCHCR@ngha.med.sa |
| iCARE Jeddah | CAREJed@ngha.med.sa |
| iCARE Al Ahsa | CAREAhsa@ngha.med.sa |
| iCARE Dammam | CAREDammam@ngha.med.sa |
| iCARE Madinah | CAREMadina@ngha.med.sa |

FIG. 23

Badge Number needs to be entered by the SN who commenced the process of iCARE Escalation

- Once Credentials of either In-Charge/Team lead/CN/NM has been entered, the assigned Primary Nurse/SN should then SAVE their documentation in BESTCare.

*This conclude the Primary Nurses documentation involvement -> further iCARE Escalation needs to be documented by In-Charge/Team lead/CN/NM, and then Physician's contribution.*

FIG. 25

- The Edited Version will open up and the In-Charge/Team lead/CN/NM needs to document the actions she/he took in trying to resolve and escalate the uncoordinated care situation.

| Wood,David | 51374 | |
|---|---|---|
| In-Charge/Teamlead/CN/NM | BN | Search |

Action Plan:
- ☑ Reviewed the Patient's medical record
- ☐ Escalated iCARE issues to NM
- ☑ Escalated iCARE issues to MRP & Co-signed
- ☐ 13h00 & no MRP/Consultant involvement yet, escalated to Division Head and/or Dept. Chairman & Co-signed
- ☐ 14h00 & iCARE issues remains unresolved, escalated to Corp. Clinical Performance & Innovation Department & Co-signed
- ☐ Other ●

FIG. 27

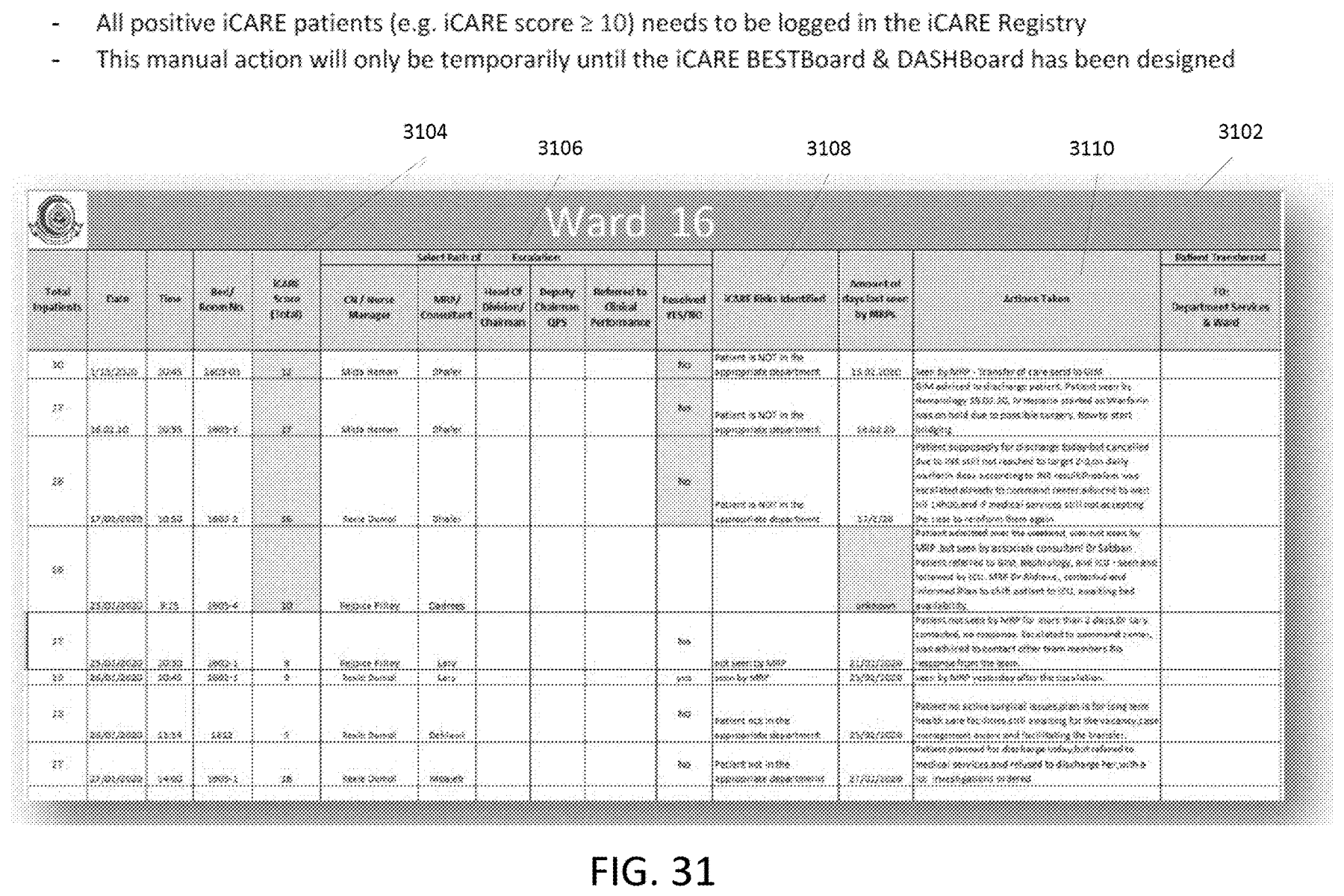

- All positive iCARE patients (e.g. iCARE score ≥ 10) needs to be logged in the iCARE Registry
- This manual action will only be temporarily until the iCARE BESTBoard & DASHBoard has been designed

FIG. 31

STEP 12: MRP & Consultant's Involvement
Once the MRP access BESTCare's Clinical Care Module via his/her access, click on the Cosign icon
- Selection of all Cosign items will appear, double click on the iCARE Departmental Form Selection
FIG. 32

- The MRP/Consultants needs to review the iCARE Risks identified and document their selection of actions that needs to be taken to resolve the Patient's identified iCARE issues.

FIG. 35

| | Diagnosis | Risk score | Risk identified | Action taken |
|---|---|---|---|---|
| 1603-03 | Vaccination | 12 | Patient not in appropriate department | Transfer of care |
| 1603-02 | Leg surgery | 17 | Patient not in appropriate department | Patient held due to possible surgery, begin moving patient |
| 1608-05 | Internal injury | 16 | Patient not in appropriate department | Escalate patient to medical services until 14:00 |
| 1605-04 | Infection | 10 | Not seen by responsible physician | Patient referred to ICU |
| 1602-01 | Internal injury | 9 | | Advanced to contact other team members |

Fig. 37

The ideal scenario is where the MRP could manage to solve all identified iCARE issues. If this is the case and all identified iCARE issues have been solved by the afternoon

- AN additional task needs to be documented by the MRP/Consultants after the actions he/she took in trying to resolve the iCARE issues
- BESTCare will automatically save all iCARE Risks that have been identified and it will be summarized as a conclusion on the bottom part of the iCARE at Risk Form
- The Physicians must document whether the Risk/s identified have been solved or not by selecting Yes/No

FIG. 38

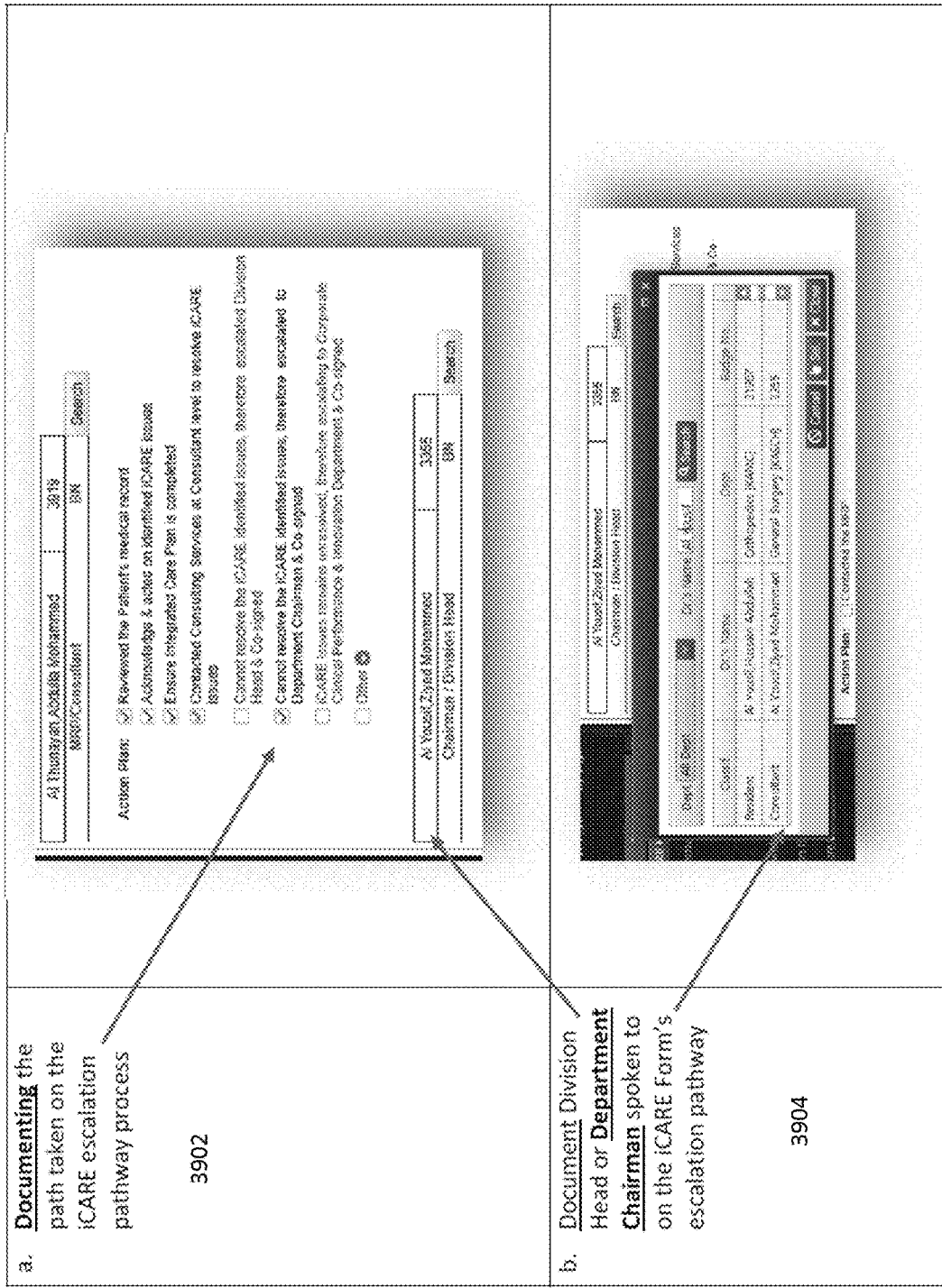

d. When reaching the Division Head or Department Chairman, they will assist in getting all iCARE issues resolved PLUS document their selection of actions that they took to resolve the Patient's identified iCARE issues

4104

4102

Al Yousif Zayed Mohammed — 3335
Chairman / Division Head — BN — Search

Action Plan:
☑ Reviewed the Patient's medical record
☑ Contacted Chairman counterparts of other involved Consultation Services regarding unresolved iCARE issues & Co-signed
☑ iCARE issues remains unresolved, therefore escalated to CCPID & Co-signed
☐ Other Dr. Azzah Thuraia - 31562
Corporate Clinical Performance & Innovation Department

FIG. 41 e. Should the Division Head and/or Department Chairman also couldn't resolve the identified iCARE issues then they have to establish contact with the Corporate Clinical Performance & Innovation Department Via:

4204 - Documentation in BESTCare

4206 - Cosign to CCPID

FIG. 42

HOSPITAL HEALTHCARE PROVIDER MONITORING AND VERIFYING DEVICE AND SYSTEM FOR PATIENT CARE CONDITION

CROSS-REFERENCE TO RELATED APPLICATIONS

The present application is a continuation of U.S. application Ser. No. 17/495,469, now allowed, having a filing date of Oct. 6, 2021 and claims the benefit of priority to U.S. Provisional Application No. 63/088,758 filed Oct. 7, 2020, the entire contents of which are incorporated herein by reference.

BACKGROUND

Technical Field

The present disclosure is directed to a healthcare provider method, system and ID device that facilitate monitoring and verifying of healthcare providers to ensure corrective actions are taken in a strict timely fashion to solve issues that lead to a risk of poorly coordinated care of a patient. The monitoring and verifying of healthcare providers includes a method for risk scoring and inpatient care coordination among specialized medical practitioners in a hospital. The risk scoring method includes steps for calculating a risk score for a risk of poorly coordinated care based on assessed criteria, and when the risk score is above a predetermined level, determining an escalation process to solve issues that lead to the poorly coordinated care. The healthcare provider ID device facilitates the escalation process by a communication link with a hospital communications system for communicating the risk of poorly coordinated care to the hospital administration hierarchy.

Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

US 2015/0213224, to R. Amarashingham et al., describes a holistic hospital patient care and management system. The system includes at least one predictive model including a plurality of weighted risk variables and risk thresholds in consideration of the clinical and non-clinical data and configured to identify at least one medical condition associated with patients.

US 2014/0379363, to C. F. Hart et al., describes patient readmission risk assessment. A patient risk score may be calculated and used to determine a likelihood of readmission of a patient. The reference indicates that being able to identify which patients contribute to a quality metric, identify admissions scenarios that may negatively affect a health care provider's quality score, and being able to determine a likelihood of readmission of a patient early in the revenue cycle may be advantageous for health care providers. US 2019/0336085, to S. Kayser et al., describes an apparatus for assessing medical risks of a patient and includes an analytics engine and equipment that provides data to the analytics engine. The analytics engine analyzes the data from the equipment to determine a sepsis risk score, a falls risk score, and a pressure injury score.

US 2014/0214441, to D. C. Young et al., describes a care management system for improving the care of a client who is supported by a caregiver. A risk analyzer may determine the client's risk for different risk conditions, and may calculate domain-specific and overall risk scores for the client. The risk analyzer may analyze the information stored by the caregiver and care management team in the data storage mechanism, in order to evaluate the client for risks of particular conditions, and moreover for an overall risk of negative outcomes. The risk analyzer may make recommendations for actions to be taken by the client, the caregiver, or the care management team in order to improve the client's care.

The risk analyzer of the '441 patent application may make recommendations for actions to be taken by the client, the caregiver, or the care management team in order to improve the client's care. However, the '441 patent as well as the other aforementioned references do not provide a solution to an urgent problem in the field of medical care. Conventional methods used in medical service centers such as hospitals are unable to assess or objectively characterize poorly coordinated care and thus are unable to effectively improve communication among clinicians to address poorly coordinated care when it occurs. There is a need to provide real time monitoring of an individual patient's risk of poorly coordinated care and a method of escalating issues related to poorly coordinated care to appropriate decision makers in a hospital.

It is one object of the present disclosure to describe a system and method that empowers nurses and junior medical staff to raise concerns about any compromise to the coordination of patient care. The system and method empower patients to receive attention and feedback regarding any concerns they have with regard to the coordination of their care. The system and method minimizes the risk of poor medical outcomes by ensuring patients are treated under the appropriate service/consultant for their current clinical needs in a strict timely fashion.

SUMMARY

An aspect of the present disclosure relates to a hybrid ID system for a medical practitioner and patient care. The system can include a hybrid electronic ID/key including a transmitter device having circuitry for storing ID data and transmitting a signal containing the ID data, and a key having a predetermined shape on a surface of the hybrid electronic ID/key; a radio frequency receptor device having circuitry, storing location information, for detecting the signal containing ID data, a matching detection section configured to match the predetermined shape of the key, and a movement tracking portion to track movement of the predetermined shape as the key is rotated; and a computer system including a patient database. The computer system configured to receive the ID data in conjunction with the location information from the radio frequency receptor device when the predetermined shape is completely rotated to a final position, and store the ID data, location information, together with patient data associated with the location.

A further aspect of the present disclosure relates to a hybrid ID system for a medical practitioner and care of a patient. The system can include a hybrid electronic ID/physical key including a radio frequency emission device having circuitry for storing ID data and transmitting a signal containing the ID data, and a physical key having a predetermined shape that protrudes from a surface of the hybrid electronic ID/physical key, the protruding predetermined shape includes a notched portion; a radio frequency receptor device having circuitry, storing location information, for detecting the signal containing ID data, a depression that matches the protruding predetermined shape of the physical key, and a cavity in which the notched portion can move through when the protruding predetermined shape is rotated in the depression; and a computer system including a patient database. The computer system configured to receive the ID data in conjunction with the location information from the radio frequency receptor when the protruding predetermined shape is completely rotated to a position in which the notched portions comes into contact with an end of the cavity, and store the ID data, location information, together with patient data associated with the location in the patient database.

A further aspect of the present disclosure relates to a hybrid ID system for a medical practitioner and patient care. The system can include a mobile device including memory for storing ID data, a first radio signal transmission device for communicating a first radio signal containing the ID data, a second radio signal transmission device having circuitry configured to communicate a second radio signal at a power and frequency for communication at a distance that is shorter than the first radio signal, a third radio signal transmission device having circuitry configured to communicate a third radio signal at a power and frequency for communication at a distance that is shorter than the second radio signal, an orientation measuring device, and processing circuitry configured to perform a mobile application; a radio frequency transmission device having circuitry, storing location information, for transmitting the second radio signal containing the location information. The mobile application configured to detect a predetermined movement gesture, using the orientation measuring device, and a predetermined distance range to the radio frequency transmission device based on the second radio signal. A computer system including a patient database, is configured to receive the ID data, via the first radio signal, in conjunction with the location information from the radio frequency transmission device when the mobile application detects the predetermined movement gesture and the predetermined distance range, and store the ID data and location information, together with patient data, transmitted via the third radio signal, for a patient.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 6 is an exemplary communication protocol for escalation of the patient risk assessment;

FIG. 15 illustrates an exemplary screen that may be displayed as a result of selecting the medical forms icon in accordance with an exemplary aspect of the disclosure;

FIG. 16 illustrates a section of the risk assessment form containing fields for entering information about the healthcare provider;

FIG. 17 illustrates a section of the risk assessment form containing fields for entering information about a patient;

FIG. 18 illustrates an exemplary risk assessment questions section to assess poorly coordinated care for a particular hospital department in accordance with an exemplary aspect of the disclosure;

FIG. 19 illustrates an exemplary sub-question for a risk criteria that requires further explanation;

FIG. 20 illustrates an exemplary sub-question for a risk criteria that requires further explanation;

FIG. 23 is an exemplary escalation process for a department in accordance with an exemplary aspect of the disclosure;

FIG. 25 is a step of co-signing by a charge nurse or nurse manager in accordance with an exemplary aspect of the disclosure;

FIG. 27 illustrates a portion of an edited version of the risk assessment form in accordance with an exemplary aspect of the disclosure;

FIG. 31 illustrates a risk assessment registry that contains a record of all patients that have been subject to a risk assessment;

FIG. 32 illustrates options that the responsible physician will be provided once notified of a request for cosign;

FIG. 35 illustrates a portion of an interface for a responsible physician that includes a list of checkboxes for actions that the responsible physician may choose to take in order to resolve the patient's unresolved risk assessment issues;

FIG. 37 is\illustrates an exemplary matrix for the recommender system;

FIG. 38 illustrates an exemplary summary of risks identified and whether they have been resolved;

FIG. 39 illustrates a subsequent escalation process in a case where the responsible physician was not able to solve all risk assessment issues within the required time period;

FIG. 41 illustrates a portion of a screen that may be displayed to the recipient of the cosign request; and FIG. 42 illustrates a further escalation process that may occur when the department chairmen could not resolve identified risk issues;

DETAILED DESCRIPTION

Figure 1:
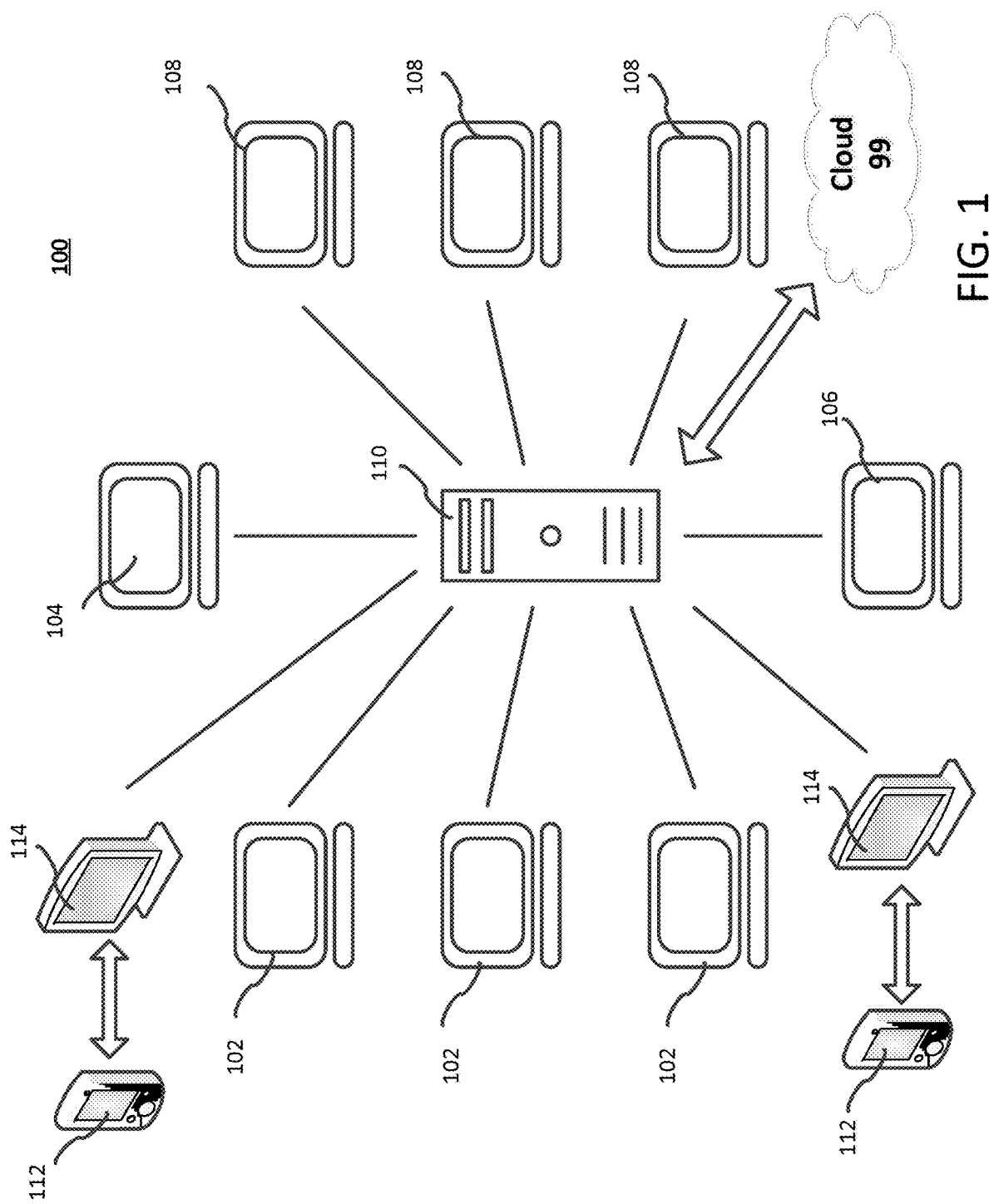
FIG. 1 is a system diagram of Risk Scoring for Patient Care Condition in an exemplary hospital.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

Hospital medical care is becoming vastly more sophisticated and highly specialized. This creates a challenge and a need for an enhanced level of coordination of care among highly specialized medical teams to ensure that the patient stays at the center of the care. In some cases, a patient may be briefly checked on by a physician during an initial consultation. During a patient's stay, nurses often follow routine practices to check on the condition of a patient and the patient may assume that the quality of care is appropriate for the medical condition. Often a patient may rate their service upon completion of their hospital visit.

However, there may be cases where the nurse that regularly checks the condition of the patient and the patient have concerns about the initial diagnosis or the manner that the medical condition progresses during the hospital stay. Possibly, the nurse and/or patient may believe that the patient should be reviewed by a different physician, should receive a different treatment, or should receive a more aggressive treatment. In other words, something in the treatment protocol may need to be revised, and the nurse and/or patient may need a resource to bring this concern to an appropriate clinician. Possibly a nurse or patient needs assistance in evaluating the treatment plan as it is being performed, rather than when it is completed according to regular practice.

A hospital is typically a large organization which may house hundreds of patients and may be served by various nurses, nurse managers and physicians in several departments. Specialized departments may include Adult Critical Care, Peds Critical Care, Neonatology Critical Care, Cardiac Sciences, Medical Services, General Surgery, Peds Surgery, Orthopedics Surgery, Plastic Surgery, Neurosurgery, Urology Surgery, Thoracic Surgery, Ophthalmology Surgery, Vascular Surgery, ENT Surgery, Podiatric Surgery, Neurology/Stroke, OB/GYNE, Gynecology Oncology, Hematology, Mental Health, Neonatology, Oncology, Organ Transplant, and others.

The hospital may assign a patient to one department for care based on an initial consultation with a physician or other consultant who may be part of an organization that is separate from the hospital, such as an urgent care facility or a patient primary care physician, or with a physician or other consultant that is resident at the hospital. Such an initial consultation is the primary method of making a decision as to which department the patient is to be assigned. The department may be a general department that covers a range of medical conditions or may be a department for a specific medical procedure.

A patient may be assigned to a room in a department and may stay in that department for several days or even weeks depending on the extent of a medical condition. During the stay, a nurse may visit the patient while making a routine round to several other patients in the department. The visit may be a visit during a certain time of day, such as morning, afternoon, evening. During this routine visit, patient vital signs may be checked and recorded, and the nurse may ask the patient general questions such as how they are feeling. In some cases, the nurse may make a visual inspection of the patient if the medical condition includes external symptoms.

In some cases, the patient may express and/or inform medical staff of additional symptoms that have become evident or come to mind during the early period of the hospital stay, that were not previously noted. A patient may express changes in medical condition or symptoms that may have developed during a hospital stay or may evolve during the stay. The initial course of action during this period of change may be to simply keep an eye on the patient and monitor the change. During this same period, a physician may stop by to check on the patient and ask general questions, depending on the medical condition of the patient and the availability of a physician in the department. In some cases, a physician for the department may be busy with another patient and may not have time to visit with some patients in the department until later.

This unstructured visitation by physicians despite changes in the medical condition of a patient may be based on whether the nurse has taken action to locate the physician and request a visitation. The limited number of physicians in the department, and specialized physicians being located in other departments leads to a condition in which a patient competes with other patients for the limited access to a physician. It may be the case that it is up to the patient themselves or a nurse to make a determination that a certain specialist physician should be consulted, priority should be given to the patient based on the change in medical condition, and/or that the patient should be moved to another department.

Priority to see a specialist physician may be based on qualitative factors, such as how close a physician is to a patent's room, or that the physician is on or off duty during a time period. The patient certainly cannot make this decision. The primary nurse may not be capable of making the decision.

FIG. 1 is a system diagram for an exemplary hospital computer network. The computer system in FIG. 1 is a centralized network system 100 in which various terminals are connected to a centralized computer system 110. However, it should be understood that a hospital computer network may take on other configurations, such as connections to a computer system that is located outside of the hospital, or a hierarchical arrangement in which groups of terminals are connected to local computer servers, and the local computer servers are interconnected or connected to the centralized computer system 110.

Groups of terminals may be located in each hospital department. A terminal may be a computer system that is dedicated to one type of user, or may be a computer system that can be accessed by different types of users, where each user may be authorized to view certain data interfaces. For example, a primary nurse may be authorized to view medical information about a patient, while a nurse manager may be authorized to view management information about primary nurses, as well as medical information about patients in a department. A nurse manager may have access to reports that primary nurses cannot retrieve or view.

Referring to FIG. 1, different terminals are shown for different types of users for ease of understanding. Such terminals may be the same or different physical computer system. Computer terminals 102 may be computer systems or client terminals located in each patient room. Client terminals 102 may be associated with a particular hospital bed. The computer terminals 102 may be primarily accessed by a primary nurse, but may be used by a managing nurse or physician provided entry of appropriate authorization information which may be entered into specific user interfaces that have been set up based on the type of user. Computer terminals 108 may be located in offices that are used by physicians or managing nurses, or in shared office space for use outside of a patient room. Computer terminal 104 may be located in an administrative office, for example an office of a department chair or other hospital administrator. Computer terminal 106 may be located in another administrative office.

The hospital computer network 100 may have a connection to an external environment, such as a wide area network that connects to other hospitals in a hospital group, and/or a connection to regional medical facilities, and/or a connection to the Internet. In each case, the connections to an external environment would typically be secure connections. In addition connections to an external environment may be wired or wireless connections.

In addition to various computer terminals 102, the hospital computer network 100 may include support services, such as printers, scanners, medical imaging machines, X-ray machines, and other special purpose medical hardware devices. In some embodiments, healthcare providers, including primary nurses, charge nurses, responsible physicians, and nurse managers may be provided with a computer-readable tag device 112 that can be read by a tag reading device 114. The tag device 112 may be as simple as an RFID device, a mobile device having near field communications, Bluetooth, or WiFi capabilities. The tag reading device 114 may be a RFID reader, a device with near field communication, Bluetooth, or WiFi, or a scanner for reading a bar code, a magnetic strip, or other form of close range data transmission.

Figure 2:
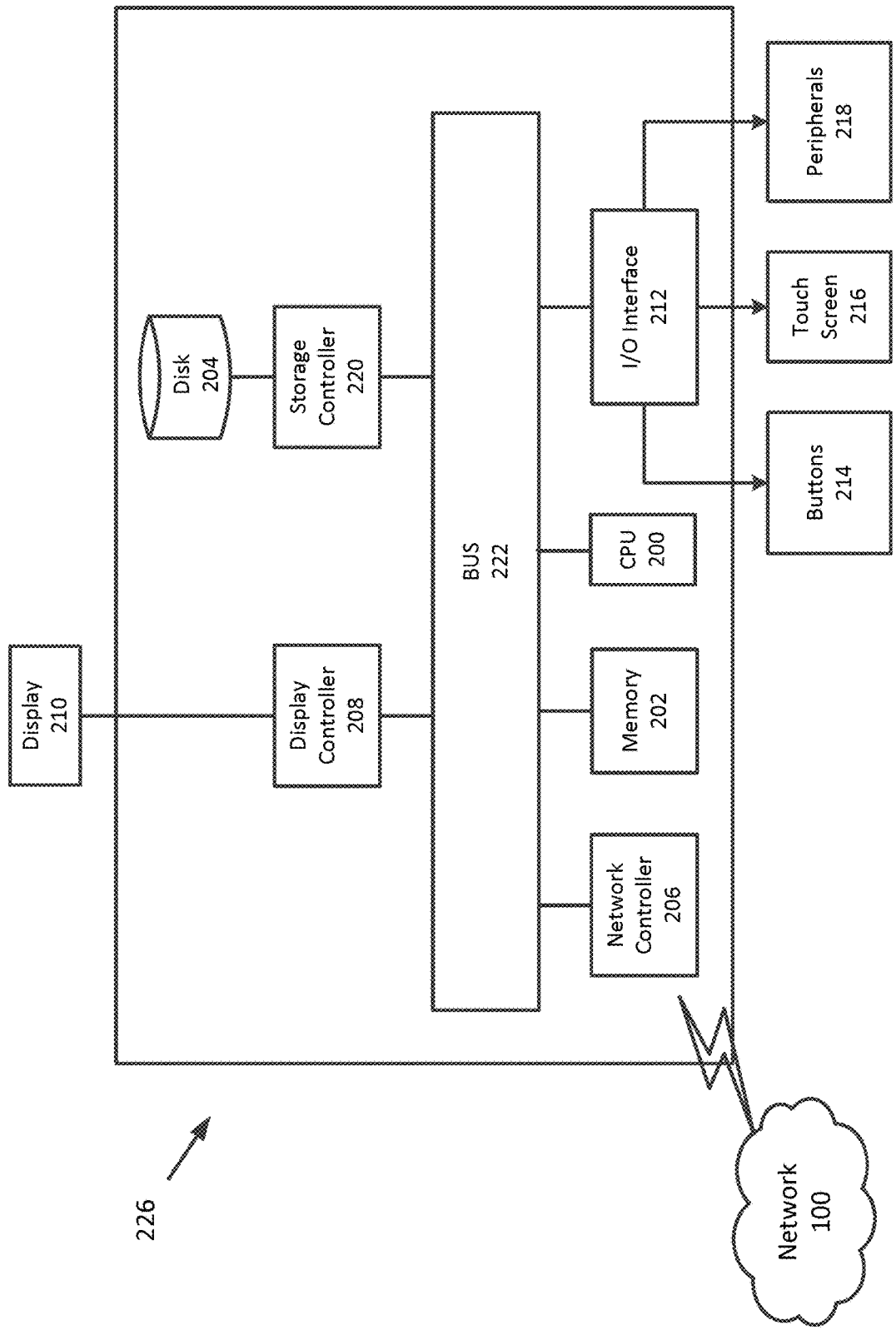
FIG. 2 is a block diagram of a general purpose computer in the system of FIG. 1.

FIG. 2 is a block diagram for a general purpose computer that may represent basic components of a computer terminal 102, 104, 106, 108, as well as a server 110.

In one implementation, the functions and processes of the computer terminal 102, 104, 106, 108 or server 110 may be implemented by a computer 226. Next, a hardware description of the computer 226 according to exemplary embodiments is described with reference to FIG. 2. In FIG. 2, the computer 226 includes a CPU 200 which performs the processes described herein. The process data and instructions may be stored in memory 202. These processes and instructions may also be stored on a storage medium disk 204 such as a hard disk drive (HDD) or portable storage medium or may be stored remotely. Further, the embodiments are not limited by the form of the computer-readable media on which the instructions of the inventive process are stored. For example, the instructions may be stored on CDs, DVDs, in FLASH memory, RAM, ROM, PROM, EPROM, EEPROM, hard disk drive or any other information processing device with which the computer 226 communicates, such as a server or computer.

Further, patient risk assessment operations may be provided as a utility application, background daemon, or component of an operating system, or combination thereof, executing in conjunction with CPU 200 and an operating system such as Microsoft® Windows®, UNIX®, Oracle® Solaris, LINUX®, Apple macOS® and other systems known to those skilled in the art.

In order to achieve the computer 226, the hardware elements may be realized by various circuitry elements, known to those skilled in the art. For example, CPU 200 may be a Xenon® or Core® processor from Intel Corporation of America or an Opteron® processor from AMD of America, or may be other processor types that would be recognized by one of ordinary skill in the art. Alternatively, the CPU 200 may be implemented on an FPGA, ASIC, PLD or using discrete logic circuits, as one of ordinary skill in the art would recognize. Further, CPU 200 may be implemented as multiple processors cooperatively working in parallel to perform the instructions of the inventive processes described above.

The computer 226 in FIG. 2 also includes a network controller 206, such as an Intel Ethernet PRO network interface card from Intel Corporation of America, for interfacing with hospital computer network 100. As can be appreciated, the hospital computer network 100 can be a public network, such as the Internet, or a private network such as LAN or WAN network, or any combination thereof and can also include PSTN or ISDN sub-networks. The hospital computer network 100 can also be wired, such as an Ethernet network, or can be wireless such as a cellular network including EDGE, 3G, 4G and 5G wireless cellular systems. The wireless network can also be WiFi®, Bluetooth®, or any other wireless form of communication that is known.

The computer 226 may further include a display controller 208, such as a NVIDIA® GeForce® GTX or Quadro® graphics adaptor from NVIDIA Corporation of America for interfacing with display 210, such as a Hewlett Packard® HPL2445w LCD monitor. A general purpose I/O interface 212 interfaces with a keyboard and/or mouse 214 as well as an optional touch screen panel 216 on or separate from display 210. General purpose I/O interface also connects to a variety of peripherals 218 including printers and scanners, such as an OfficeJet® or DeskJet® from Hewlett Packard®.

The general purpose storage controller 220 connects the storage medium disk 204 with communication bus 222, which may be an ISA, EISA, VESA, PCI, or similar, for interconnecting all of the components of the computer 226. A description of the general features and functionality of the display 210, keyboard and/or mouse 214, as well as the display controller 208, storage controller 220, network controller 206, and general purpose I/O interface 212 is omitted herein for brevity as these features are known.

Figure 3:
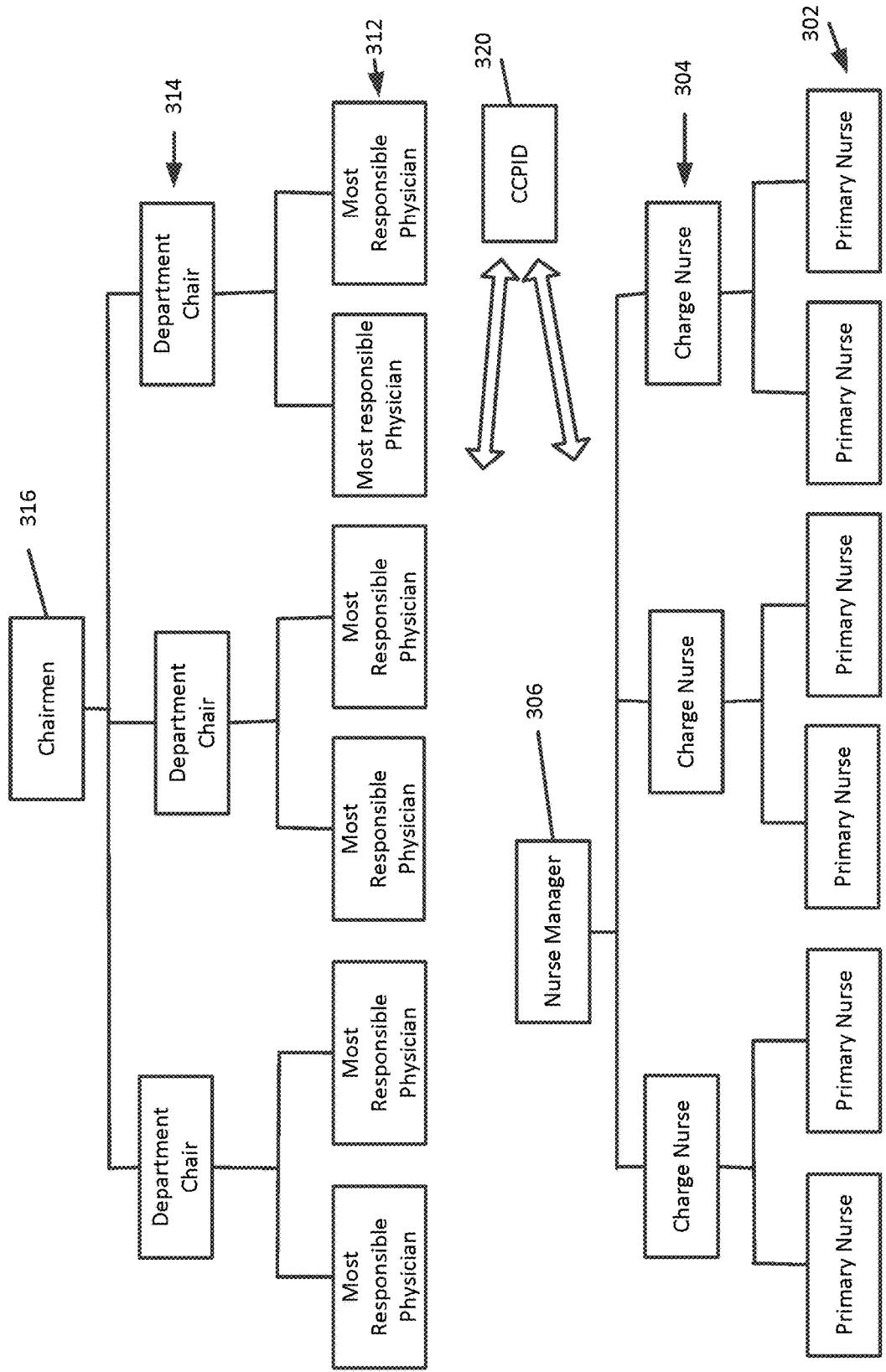
FIG. 3 is an administration hierarchy in an exemplary hospital.

FIG. 3 illustrates a hierarchy for an exemplary hospital organization. In an exemplary hospital, primary nurses 302 (also referred to as a staff nurse or bedside nurse) are healthcare providers that provide direct patient care, including monitoring, observing and assessing patients. They are the first point of contact for questions or concerns that patients may have.

They may perform duties including checking vital signs and recording the vital signs in a log for a patient so that others can view the history of a patient, and the patient history during a stay is made of record. The primary nurse 302 may provide a patient with any necessary medications. The primary nurse 302 may ask the patient questions in order to assess any change in medical condition that the patient may be experiencing. The primary nurse 302 may perform a visual check of a patient in a case that the patient has external medical conditions, such as a rash, or other changes in skin condition that may indicate a reaction to a medication. The primary nurse 302 may ask questions to obtain a general gage as to whether the patient may have a reaction to a medication, such as whether the patient feels nauseous, has any pain, soreness, stiffness, etc.

A primary nurse 302 may have advanced education and clinical training in a healthcare specialty area, and may make decisions regarding healthcare. In some cases, a primary nurse 302 may provide patient care and treatment services in collaboration with a physician.

A charge nurse 304 oversees primary nurses 302. A charge nurse 304 may generally arrange care and support for patients, as well as other tasks such as scheduling primary nurses 302 (staff nurses).

A nurse manager 306 directs patient care and provides leadership for a department.

In the exemplary hospital, responsible physicians 312 may visit with patients that have special medical conditions. Responsible physicians 312 in a hospital may be general practitioners or may be specialists in areas such as cardiologist, urologist, obstetrician, pediatrician, anesthesiologist, oncologist, to name a few.

A department chair 314 may be a physician that has had considerable experience with medical conditions that are handled in the department. The department chair 314 may manage physicians for the department.

A chairmen 316 is one that oversees hospital divisions. A chairmen 316 may have access to advice from regional services in order to provide a broad range of medical advice. Thus, higher levels of hospital administration generally have a broader range of medical knowledge and generally manage and direct actions for persons at lower levels.

Figure 4:
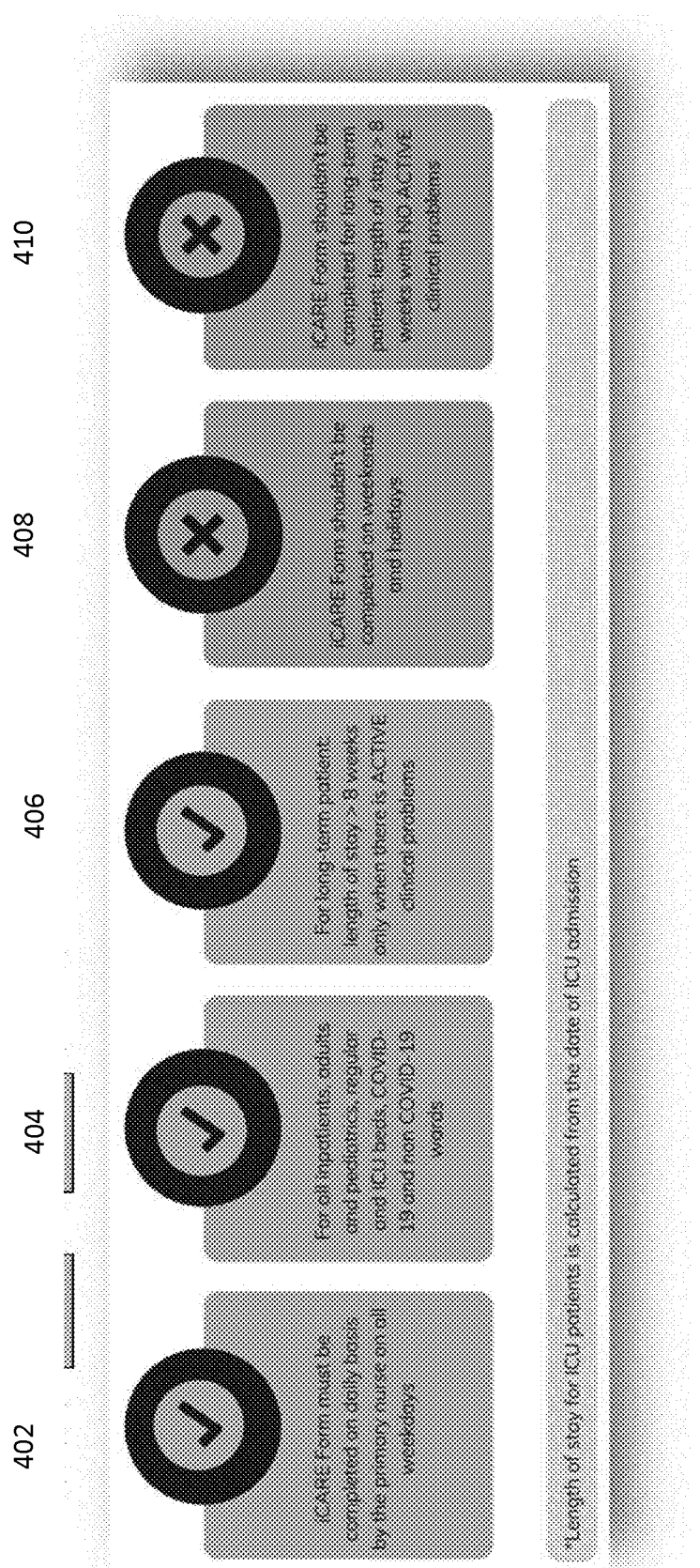
FIG. 4 is an exemplary set of conditions necessary for performing a patient risk assessment.

FIG. 4 is an exemplary set of conditions necessary for performing a patient risk assessment of poorly coordinated care. An initial risk assessment of poor performance and outcomes of the medical practice may be performed each day for each patient by a primary nurse 302. The risk assessment may lead to an assessment that is provided to the chairman 316 for those patients where issues have not been appropriately taken care of in the hospital organization in a timely fashion. There may be patients where a risk assessment may not be performed. For example, a risk assessment may not be performed during certain days or during certain periods 408, where a chairman 316 or other administration official 314 may not be accessible. A risk assessment may not be performed for a patient that is subject to long-term stay, for example, greater than eight weeks, but currently does not have critical problems 410. Otherwise, a risk assessment for poorly coordinated care may be performed each day for each patient 402. The risk assessment for poorly coordinated care should be performed for all inpatients, adults and pediatrics in both regular and intensive care unit beds 404. A risk assessment for poorly coordinated care should be performed for long-term care patients when there are active clinical problems 406.

Figure 5:
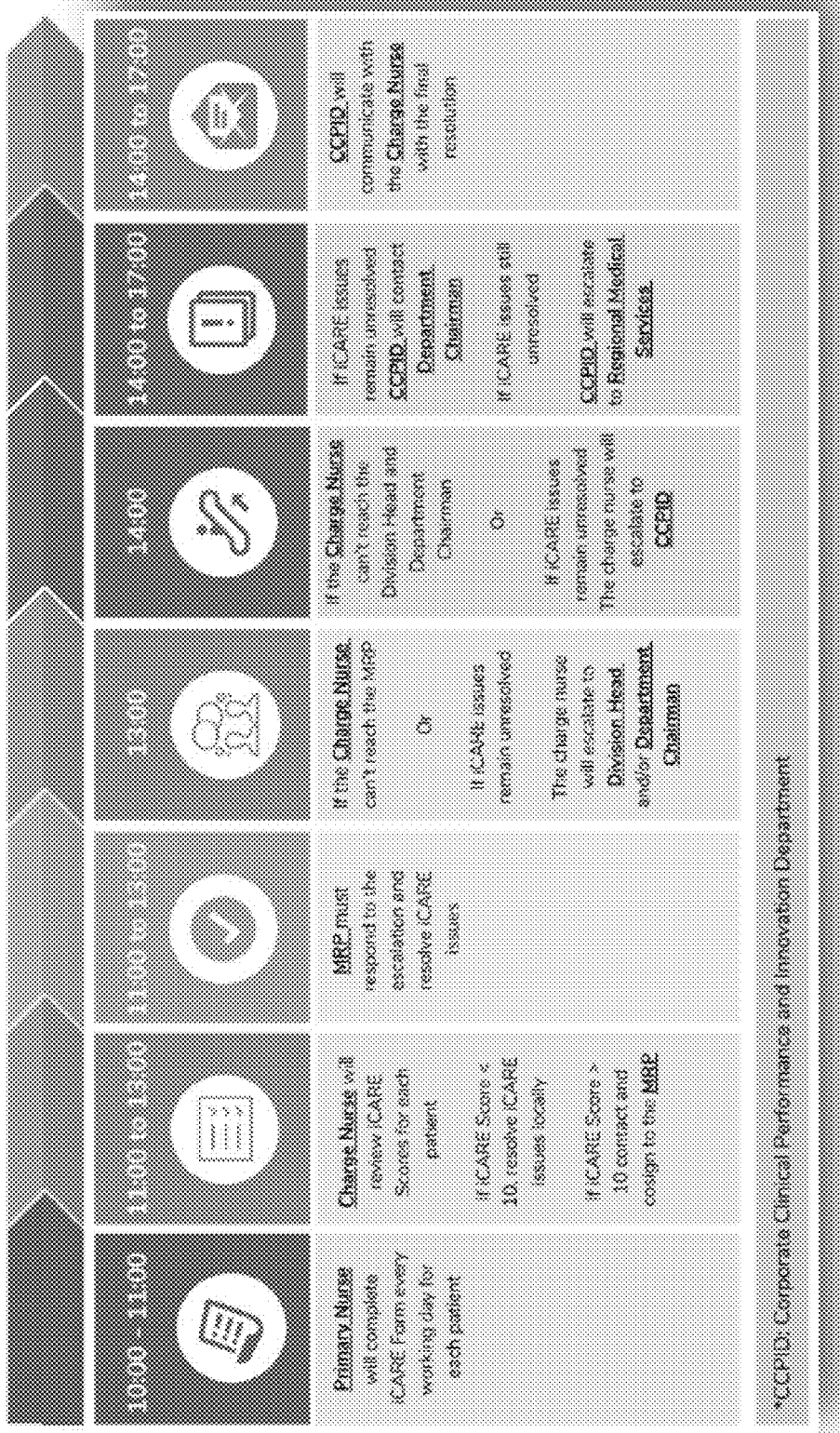
FIG. 5 is an exemplary escalation process for the patient risk assessment.
Figure 7A:
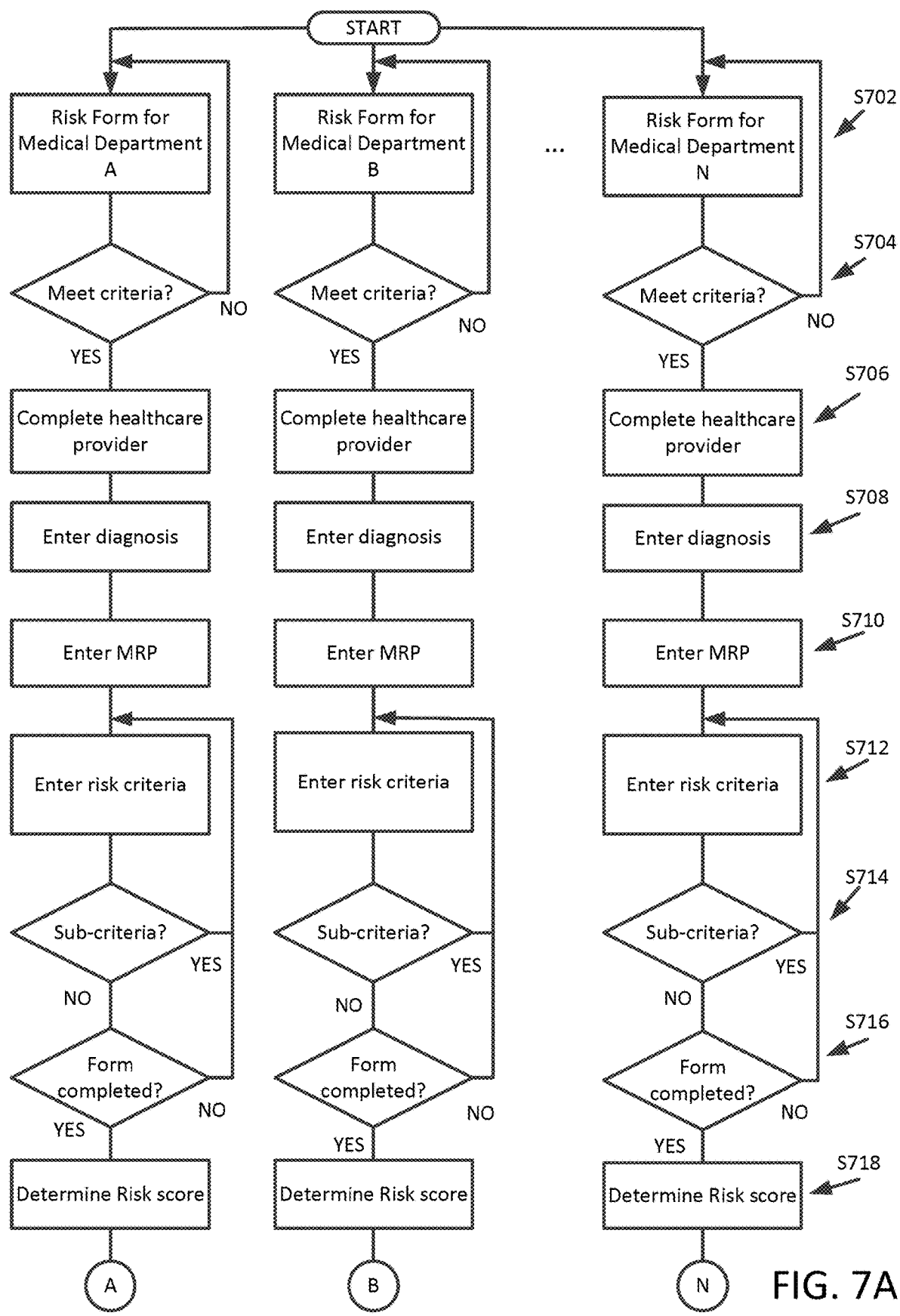
FIGS. 7A to 7D is a flowchart of patient risk assessment in accordance with an exemplary aspect of the disclosure.
Figure 7B:
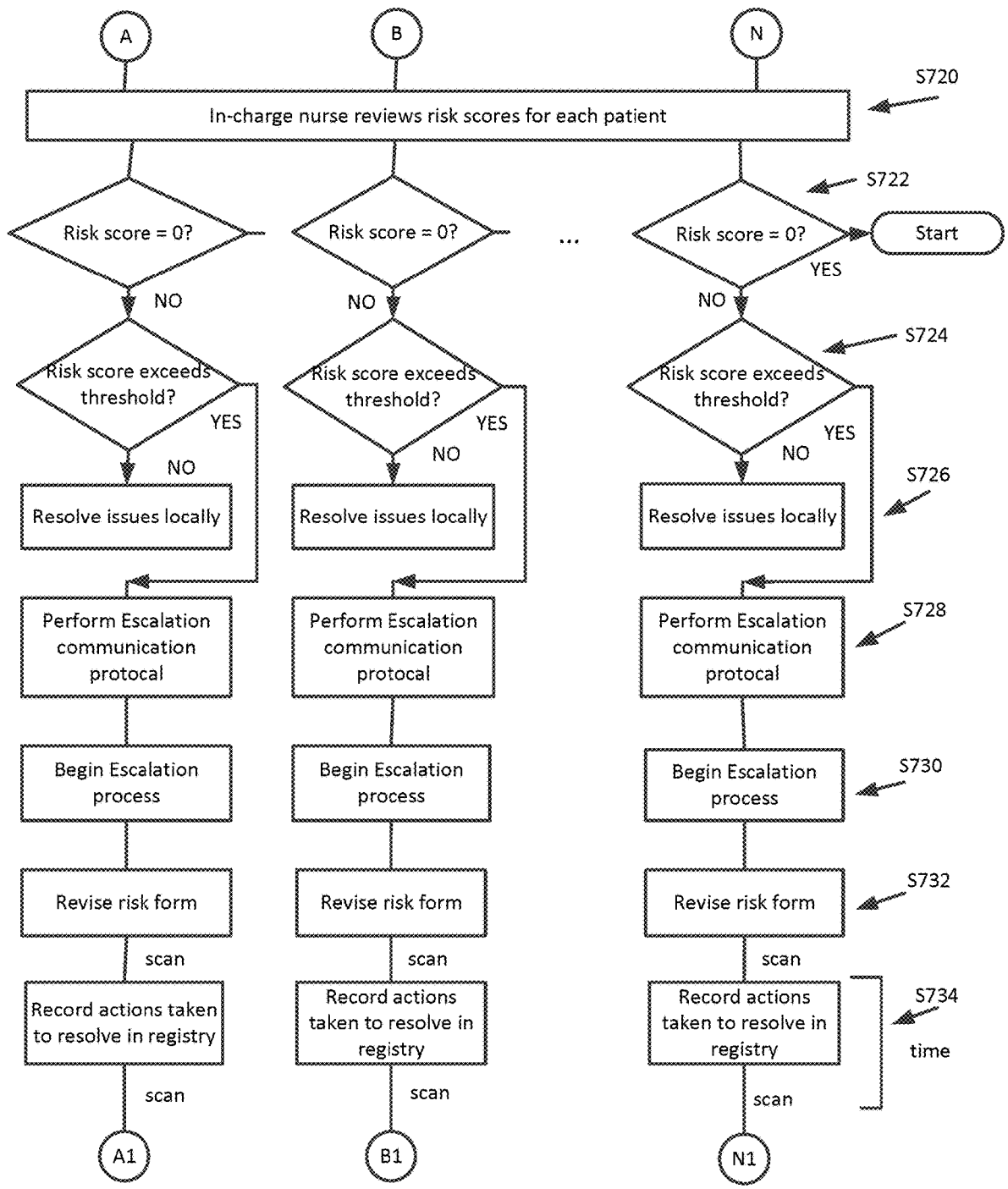
Figure 7C:
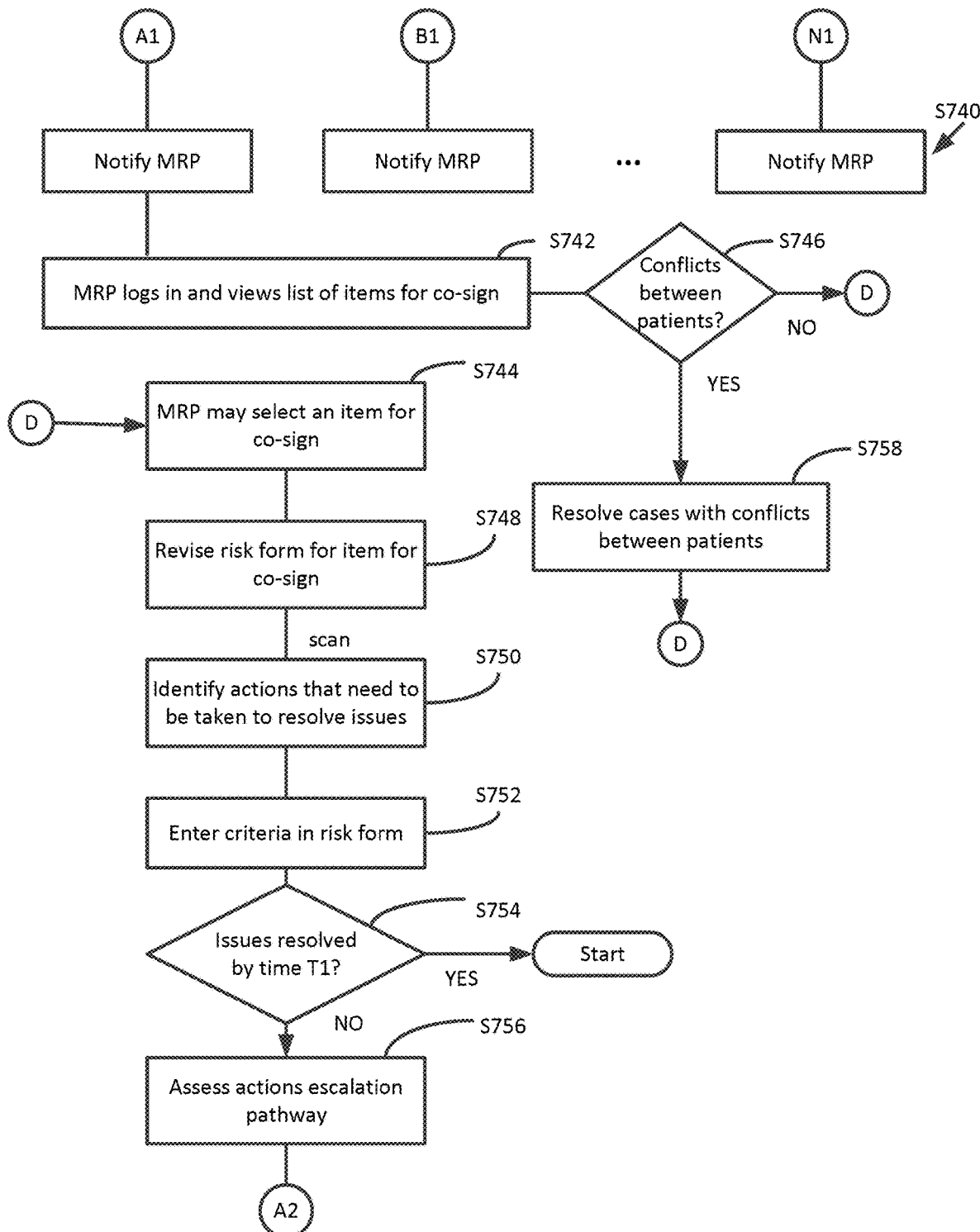
Figure 7D:
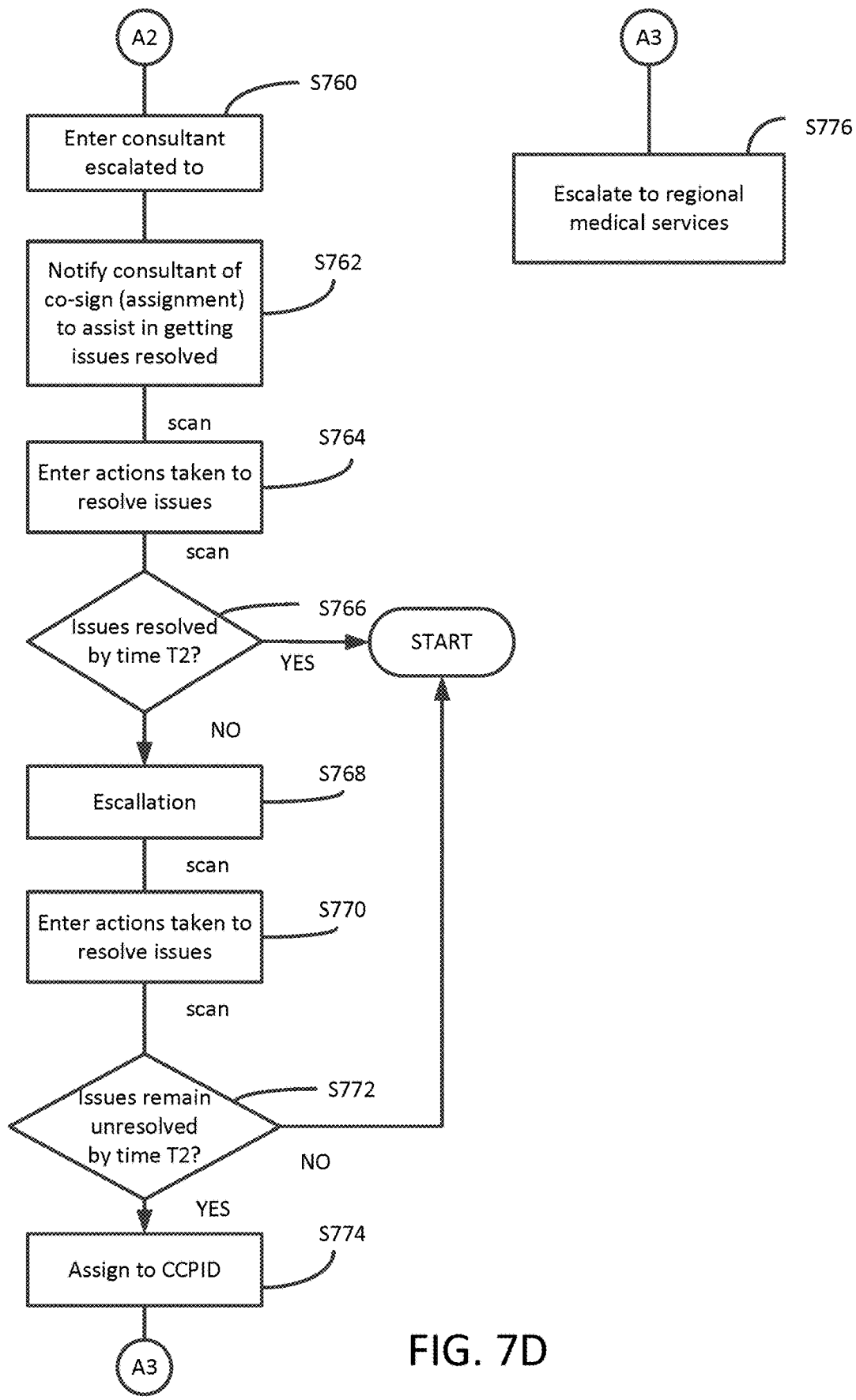

FIG. 5 is an exemplary escalation process for the patient risk assessment. In cases where the conditions for performing a risk assessment are met, in order to determine whether issues related to poor coordination among healthcare providers in a hospital are addressed in a timely fashion, a departmental escalation process may be carried out according to a strict schedule. FIG. 5 illustrates an example of such a strict schedule. The schedule may include time periods in which certain tasks must be completed. The schedule may include the healthcare provider that is responsible for the tasks during a time period. The schedule may include conditions that may be considered when addressing issues regarding the patient risk assessment. The conditions include the "if" conditions shown in FIG. 5. For example, the "if" condition "if iCARE Score <10, resolve iCARE issues locally" represents a condition that may be considered in determining a course of action. The conditions and courses of action may be configured in the form of a decision tree. The particular conditions and courses of action may vary for each condition and risk of poorly coordinated care.

Referring to FIG. 5, in 502, one or more primary nurses 302 are to complete a risk assessment form every working day for each patient. The primary nurses 302 must complete the risk assessment forms within a time period, for example between 10:00 and 11:00. In a next time period 504, the charge nurse will review risk assessment scores for each patient. The hospital computer network 100 may perform a decision process in order to determine a next course of action. In one embodiment, if the risk assessment score is less than a predetermined score, the hospital computer network 100 will instruct the charge nurse 304 that issues raised in the risk assessment form should be dealt with locally in the medical unit/ward that is the responsibility of the charge nurse 304. If the risk assessment score is greater than a predetermined score, the hospital computer network 100 will instruct the charge nurse 304 to have the issues addressed by a responsible physician 312, referred to as an escalation step. If the charge nurse 304 does not make a decision regarding a risk assessment score for a patient by the end of the time period 504, the hospital computer network 100 will automatically perform an escalation step.

In a next time period 506, the responsible physician 312 must respond to the escalation and take action to resolve issues indicated in the risk assessment form that led to the risk assessment score. Again, the responsible physician 312 must complete actions to resolve the issues within the time period 506.

If the charge nurse 304 cannot contact the responsible physician 312 within the time period 506, or the responsible physician 312 is unable to complete all of the issues within that time period 506, at time 508, the charge nurse 304 will escalate the remaining issues to a department chairmen 314. The charge nurse 304 will be given a period of time 510 to reach the department chairmen 314.

If the charge nurse 304 cannot reach the department chairmen within the time period 510, or if there are still remaining issues to be resolved, the charge nurse 304 may escalate the remaining issues to an organization (referred to as Corporate Clinical Performance and Innovation Department, CCPID 320) that will review the issues and take measures to ensure appropriate actions are taken to timely resolve the issues. That organization will contact the department chairmen 314 to determine what courses of action should be taken to resolve remaining issues with a patient(s). A predetermined time period 512 will be set for the remaining issues to be resolved. If at the end of the time period 512, there are still unresolved issues, an escalation step will occur to elevate the issue resolution to a chairmen 316 or to a regional medical service. In addition, in 514 the organization will communicate with the charge nurse 304 to inform them of the final resolution.

FIG. 6 is an exemplary communication protocol for escalation of the patient risk assessment. In one embodiment, the escalation process will be performed using a pre-established communication protocol. According to the communication protocol, in 602, when a primary nurse 302 completes a risk assessment form and a risk score is generated, the completed form and risk score will be transmitted to the central computer 110, as well as to a computer terminal 102 of charge nurse 304. In 604, the charge nurse 304 may verify the risk scores and the hospital computer network 100 will submit the risk assessment form to a computer display device associated with the responsible physician 312, such as a computer terminal 108 or mobile device 112, in accordance with an escalation step. The risk assessments that are submitted to the responsible physician are for those patients in which the risk score is above a predefined threshold score and are thus related to patients that have a high likelihood of experiencing poor care coordination. The charge nurse 304 may communicate with the responsible physician 312 in person, or by way of a phone call, video conference, text message, and/or pager.

In 606, the responsible physician 312 may communicate with the charge nurse 304 via phone or in-person visit to the department (medical ward) as appropriate.

In 608, in the case of an escalation step, a charge nurse 304 may communicate with a division chairmen 314 by way of a phone call, video conference, text message, and/or pager.

In 610, in the case of an escalation step, a charge nurse 304 may communicate with an organization (CCPID 320) that is responsible for resolving issues related to poor care coordination. The communication between the charge nurse 304 and the organization 320 may be made by way of a special direct line.

In 612, the organization (CCPID 320) may communicate with the department chairmen 316. The organization (CCPID 320), in 614, may also keep the charge nurse 304 informed by way of an e-mail, pager, phone call and/or text message.

FIGS. 7A to 7D is a flowchart of patient risk assessment in accordance with an exemplary aspect of the disclosure. The process according to the flowchart is performed by way of the hospital computer network 100, as well as other communications such as pagers and text messages. A risk assessment for poorly coordinated care provides primary nurses 302 and other junior medical staff with information that may raise concerns about any compromise to the coordination of care. The risk assessment for poorly coordinated care enables an input by a patient regarding their concerns for the coordination of their care. The risk score enables an efficient form of communication of poorly coordinated care to health care administration. The risk assessment ensures timely correction of issues that contribute to uncoordinated care, including ensuring that patients are treated under appropriate service/consultant for their current clinical needs. The risk assessment ensures that patients are reviewed at a regular interval so that senior healthcare providers are utilized with improved efficiency.

Different risk forms may be provided for each patient unit/hospital department, including Adult Critical Care, Peds Critical Care, Neonatology Critical Care, Cardiac Sciences, Medical Services, General Surgery, Peds Surgery, Orthopedics Surgery, Plastic Surgery, Neurosurgery, Urology Surgery, Thoracic Surgery, Ophthalmology Surgery, Vascular Surgery, ENT Surgery, Podiatric Surgery, Neurology/Stroke, OB/GYNE, Gynecology Oncology, Hematology, Mental Health, Neonatology, Oncology, Organ Transplant, and others.

In S702, a primary nurse 302 may log into a computer terminal 102 and select a risk assessment form that is related to the medical unit where the patient has been assigned. In S704, the risk assessment form is to be completed when the patient's stay meets certain criteria, for example criteria as shown in FIG. 4. The patient risk assessment for poorly coordinated care may be facilitated by an ID tag, such as an ID tag provided in a mobile device 112.

Types of mobile devices 112 may include a smartphone, tablet computer, laptop computer, or other computer-based device that can wirelessly connect to a computer network. In one or more embodiments, the mobile device 112 may be a computer-based device having a display device. In one or more embodiments, the mobile device 112 may include sensor devices, including sensor devices for measuring movement, position, and/or location.

In one implementation, the functions and processes of the mobile device 112 may be implemented by one or more respective processing circuits 826. A processing circuit includes a programmed processor as a processor includes circuitry. A processing circuit may also include devices such as an application specific integrated circuit (ASIC) and conventional circuit components arranged to perform the recited functions. Note that circuitry refers to a circuit or system of circuits.

Figure 8:
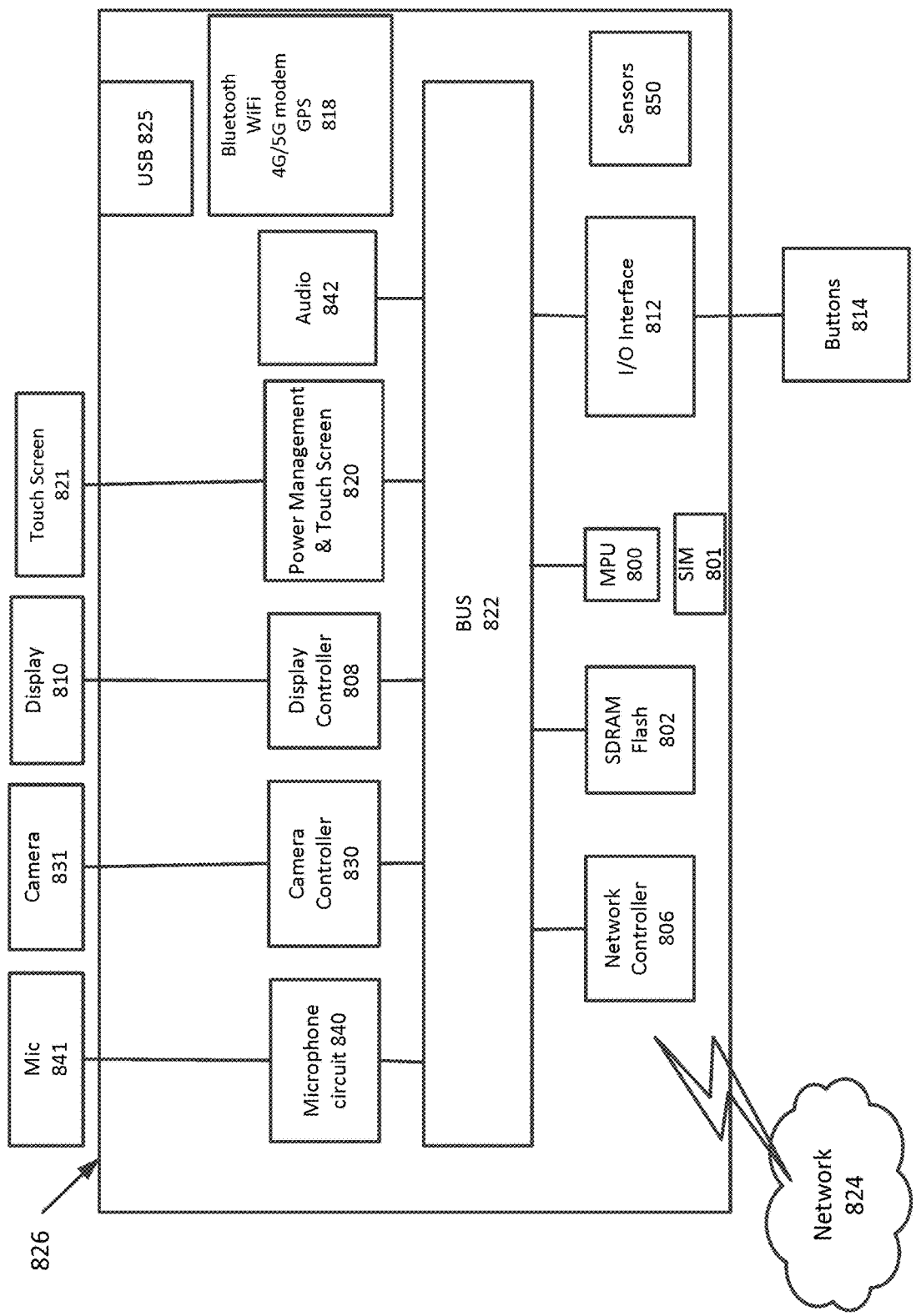
FIG. 8 is a block diagram of a general mobile device.

Next, a hardware description of the processing circuit 826 according to exemplary embodiments is described with reference to FIG. 8. In FIG. 8, the processing circuit 826 includes a Mobile Processing Unit (MPU) 800 which performs processes described herein.

The process data and instructions may be stored in memory 802. These processes and instructions may also be stored on a portable storage medium or may be stored remotely. The processing circuit 826 may have a replaceable Subscriber Identity Module (SIM) 801 that contains information that is unique to the network service of the mobile device 112.

Further, embodiments are not limited by the form of the computer-readable media on which the instructions are stored. For example, the instructions may be stored in FLASH memory, Secure Digital Random Access Memory (SDRAM), Random Access Memory (RAM), Read Only Memory (ROM), Programmable Read-Only Memory (PROM), Erasable Programmable Read-Only Memory (EPROM), Electrically Erasable Programmable Read Only Memory (EEPROM), solid-state hard disk or any other information processing device with which the processing circuit 826 communicates, such as a server or computer.

Further, embodiments may be provided as a utility application, background daemon, or component of an operating system, or combination thereof, executing in conjunction with MPU 800 and a mobile operating system such as Android, Microsoft® Windows® 10 Mobile, Apple iOS® and other systems known to those skilled in the art.

In order to achieve the processing circuit 826, the hardware elements may be realized by various circuitry elements, known to those skilled in the art. For example, MPU 800 may be a Qualcomm mobile processor, a Nvidia mobile processor, a Atom® processor from Intel Corporation of America, a Samsung mobile processor, or a Apple A7 mobile processor, or may be other processor types that would be recognized by one of ordinary skill in the art. Alternatively, the MPU 800 may be implemented on an Field-Programmable Gate Array (FPGA), Application Specific Integrated Circuit (ASIC), Programmable Logic Device (PLD) or using discrete logic circuits, as one of ordinary skill in the art would recognize. Further, MPU 800 may be implemented as multiple processors cooperatively working in parallel to perform the instructions of the inventive processes described above.

The processing circuit 826 in FIG. 8 also includes a network controller 806, such as an Intel Ethernet PRO network interface card from Intel Corporation of America, for interfacing with network 824. As can be appreciated, the network 824 can be a public network, such as the Internet, or a private network such as LAN or WAN network, or any combination thereof and can also include PSTN or ISDN sub-networks. The network 824 can also be wired, such as an Ethernet network. The processing circuit may include various types of communications processors for wireless communications including 3G, 4G and 5G wireless modems, WiFi®, Bluetooth®, GPS, or any other wireless form of communication that is known.

The processing circuit 826 includes a Universal Serial Bus (USB) controller 825 which may be managed by the MPU 800.

The processing circuit 826 further includes a display controller 808, such as a NVIDIA® GeForce® GTX or Quadro® graphics adaptor from NVIDIA Corporation of America for interfacing with display 810. An I/O interface 812 interfaces with buttons 814, such as for volume control. In addition to the I/O interface 812 and the display 810, the processing circuit 826 may further include a microphone 841 and one or more cameras 831. The microphone 841 may have associated circuitry 840 for processing the sound into digital signals. Similarly, the camera 831 may include a camera controller 830 for controlling image capture operation of the camera 831. In an exemplary aspect, the camera 831 may include a Charge Coupled Device (CCD). The processing circuit 826 may include an audio circuit 842 for generating sound output signals, and may include an optional sound output port.

The power management and touch screen controller 820 manages power used by the processing circuit 826 and touch control. The communication bus 822, which may be an Industry Standard Architecture (ISA), Extended Industry Standard Architecture (EISA), Video Electronics Standards Association (VESA), Peripheral Component Interface (PCI), or similar, for interconnecting all of the components of the processing circuit 826. A description of the general features and functionality of the display 810, buttons 814, as well as the display controller 808, power management controller 820, network controller 806, and I/O interface 812 is omitted herein for brevity as these features are known.

The mobile device 112 may include sensor devices 850. Sensor devices 850 may include an accelerometer for measuring movement and orientation, geomagnetic field sensor to determine position, a Global Positioning System for determining location, as well as other sensors for detecting environmental conditions, proximity, and light to name a few.

Figure 9:
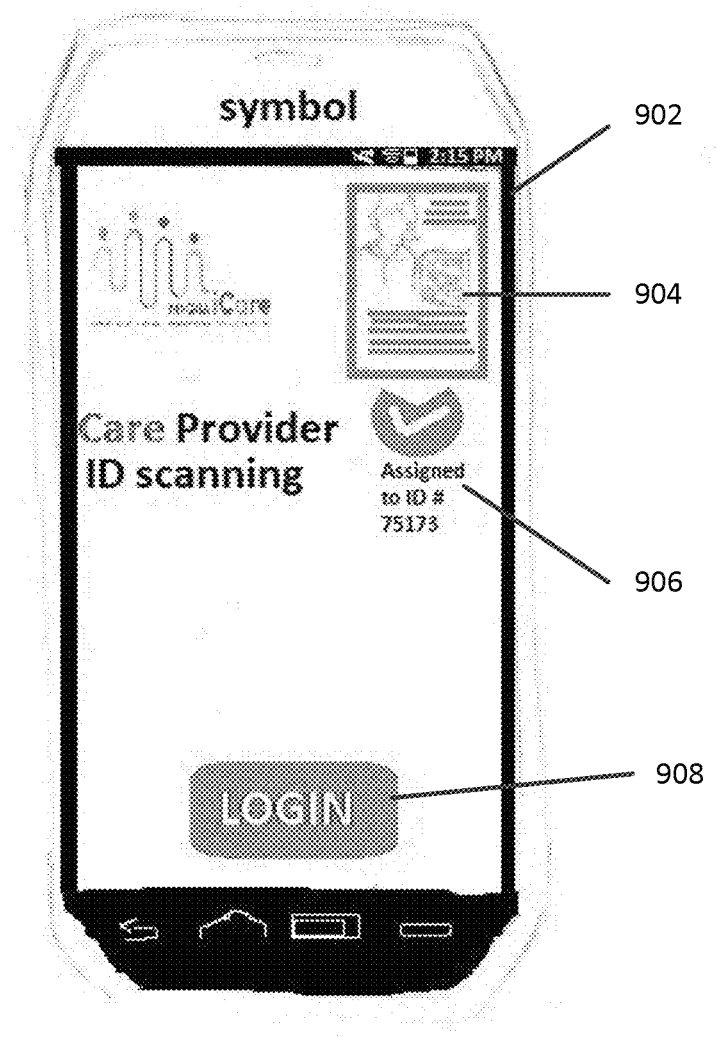
FIG. 9 illustrates an exemplary healthcare provider id tag in a mobile device in accordance with an exemplary aspect of the disclosure.

FIG. 9 illustrates an exemplary healthcare provider ID tag in accordance with an exemplary aspect of the disclosure. A healthcare provider ID tag may be an electronic badge worn by a healthcare provider and may have an embedded RFID tag detectable by an RFID reader. Alternatively, the healthcare provider may be provided with a mobile device 112 having an installed mobile application 904 (also referred to as an App), in which the mobile application 904 contains a detectable image displayed in a display device 902 associated with a tag ID. In one embodiment, the mobile application 904 may include a user login function 908 that requires that a user log into the mobile application 904 in order to authenticate the user. Once logged in, the mobile application 904 may associate the detectable image with an id 906 of the healthcare provider.

The detectable image displayed by the mobile application 904 can be a bar code (2D or 3D) that is scanned by a scanner 114, in which the scanner 114 has a fixed location that is used to identify the location of the healthcare provider and a time that the healthcare provider enters the location. The detectable image may again be scanned when the healthcare provider exits the location having the scanner 114. The mobile application 904, once the healthcare provider has logged in, will establish a link to a patient's electronic medical record for a patient staying at the location (hospital room). The link may be by way of a wireless link to the hospital central computer system 110, or may be by way of a communication link with a computer terminal 102 in a hospital room. In the case that more than one patient is staying in a hospital room, the link to a patient's medical record will be based on a terminal 102 that is associated with a particular hospital bed. The link also establishes a connection to a risk assessment form for a patient. The link may be configured to cause identification information of the healthcare provider to be populated in a risk assessment form.

Figure 10:
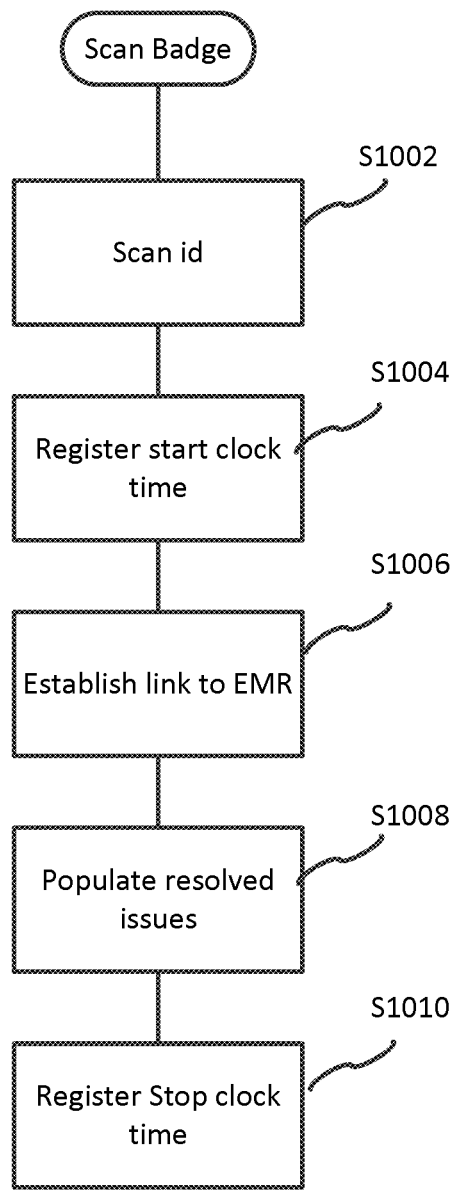
FIG. 10 is a flowchart of a scan process for the healthcare provider id tag in accordance with an exemplary aspect of the disclosure.

FIG. 10 is a flowchart of a scan process for the healthcare provider id tag in accordance with an exemplary aspect of the disclosure. In one embodiment, the scanner 114 and mobile application 904 perform a scanning and communication process that may be used to facilitate steps in the patient risk assessment. When a healthcare provider begins a task that may result in a step in an escalation process, in S1002, the healthcare provider first scans the id tag with scanner 114, for example an id tag displayed in the mobile application 904. Upon scanning the id tag, in S1004, a clock of the mobile application 904 registers a start time (for example, a time that a healthcare provider first enters a patient room). In addition, in S1006, the mobile application 904 establishes a link with the electronic medical record for a patient. As mentioned above, the link may be a wireless connection to the central computer system 110 or via a computer terminal 102. The link triggers automatic information about the healthcare provider to be entered into forms maintained in the central computer system 110. As actions are taken by a healthcare provider, the healthcare provider may check off issues related to the risk assessment form that are addressed. In S1008, an action taken by the healthcare provider to resolve an issue associated with the risk assessment may be checked in the risk assessment form as a resolved issue. In S1010, the mobile application will register a stop time that the resolved issue is checked in the risk assessment form.

In some embodiments, dual or triple verification of a patient visit by a healthcare provider may be used to ensure that the healthcare provider has visited the patient within an allotted time constraint to address one or more issues related to poor coordination of patient care. Proper recordation of physician identification, nurse identification or other healthcare provider identification is complemented through the use of an ID badge system that permits both electronic and physical verification of identification of the healthcare provider. Healthcare providers involved in care of a patient may be assigned a "practitioner ID badge" that permits virtual identification and tracking of a healthcare provider, and physical confirmation of identification and inpatient visitation.

Figure 11:
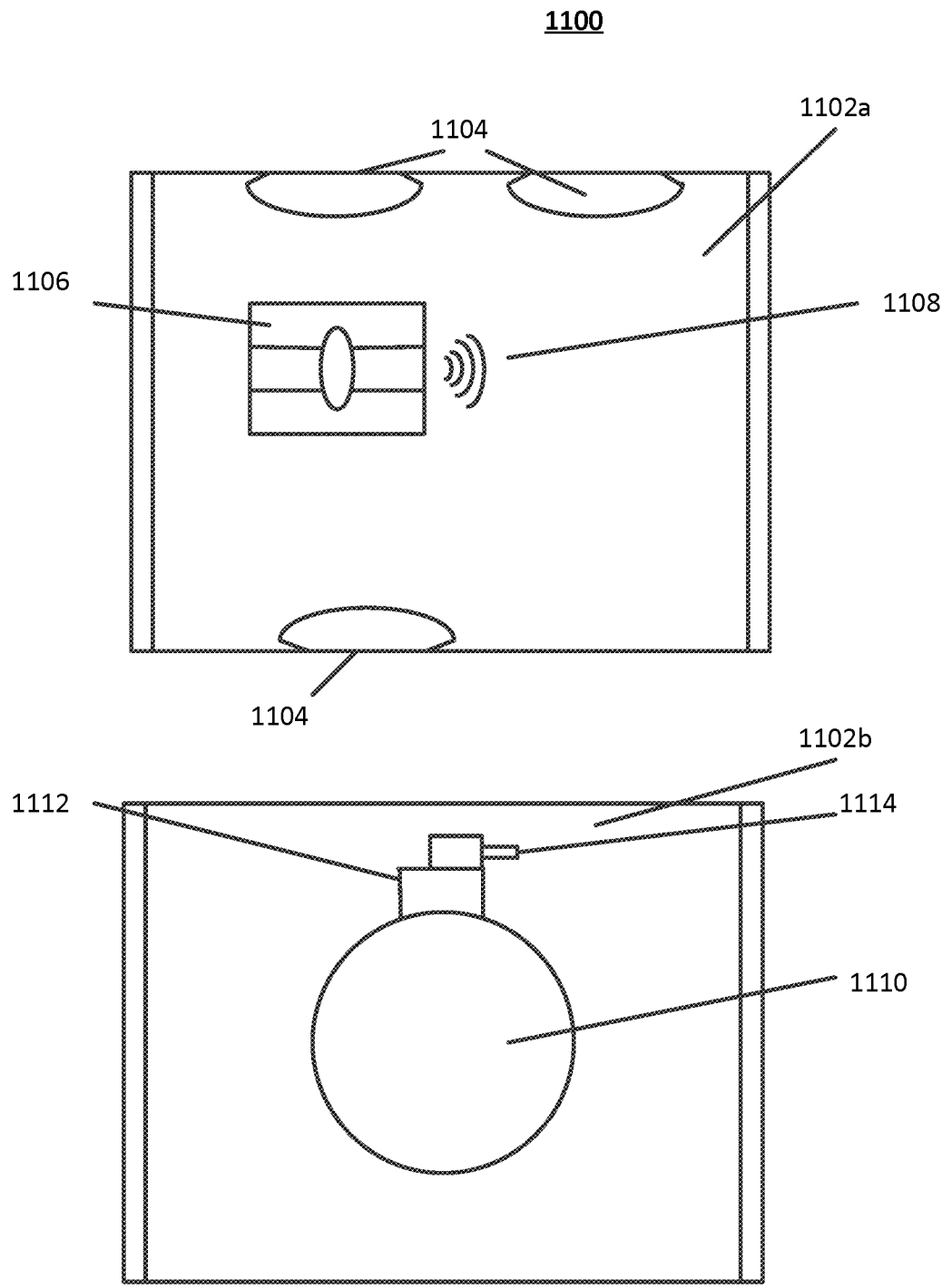
FIG. 11 is a schematic diagram of an exemplary electronic ID badge having a physical key in accordance with an exemplary aspect of the disclosure.
Figure 12:
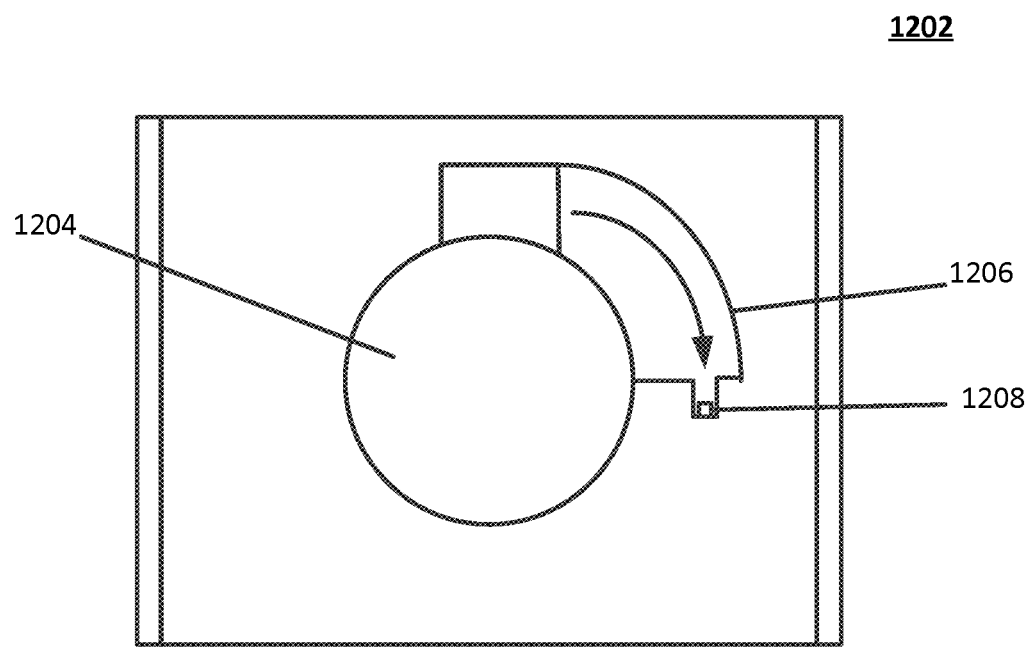
FIG. 12 is a schematic diagram of an ID badge receptor device in accordance with an exemplary aspect of the disclosure.

FIG. 11 is a schematic diagram of an exemplary electronic ID badge having a physical key. FIG. 12 is a schematic diagram of an ID badge receptor device. For electronic verification of identification of the healthcare provider, the electronic ID badge 1100 may be configured with an RFID tag 1106, embedded within one side 1102a, that can emit a radio signal 1108. In one embodiment, the RFID tag 1106 may be a passive device that emits a radio signal 1108 when interrogated by an RFID receptor device. that the RFID tag 1106 facilitates constant monitoring of a healthcare provider throughout the hospital facility on a full-time basis.

The RFID tag 1106 may be detected and monitored throughout the hospital environment with RFID detectors preferably located at average chest height at every doorway. Upon approaching a doorway, a practitioner's ID tag 1100 can be detected and recorded by the RFID detector then transmitted to the central computer system 110 by wireless or direct electronic connection and stored in a database.

For physical verification, the ID badge may also include a physical key 1110, having a specific shape, or an electronic pattern having a particular orientation. The physical key may be located on the back surface 1102b of the ID badge 1100. The physical key shape is a circular protrusion from the back surface of the ID badge. The outer circumference of the top surface of the circular protrusion may include a notched portion 1112 such that the ID badge 1100 must be oriented in a particular orientation in order to fit an ID badge receptor device 1202 located on or near the patient. The notched portion 1112 may include an electrical contact 1114.

When a clinician or healthcare provider, preferably a physician, interacts with a patient the physician first initiates a recordation of the physician's visit to the patient by locking into a matching receptacle on or near the patient. The matching receptacle, of the ID badge receptor device 1202, is a circular depression 1204 that matches the diameter of the circular protrusion 1110 on the back 1102b of the ID badge 1100. In particular, the physician first places the circular protrusion 1110 in the depression 1104 then turns the ID badge 1100 in order to "lock in" and verify that the physician's visit to the patient is being recorded. Typically a quarter turn of the ID badge 1100 is needed in order to trigger recordation of the physician's visit. The electrical contact 1114 may move during the turn within a cavity 1206 to be brought into contact with a mating electrical contact 1208 of the ID badge receptor device 1110. The ID badge 1100 may have indents 1104 on one side 1102a to assist in grasping the ID badge 1100 when turning the ID badge 1100.

In embodiments of the invention physical recordation of the physician's visit is carried out only during an escalation process. Physical recordation makes a clear record that issues regarding lack of coordination of care are receiving direct and personal attention of a physician.

Figure 13A:
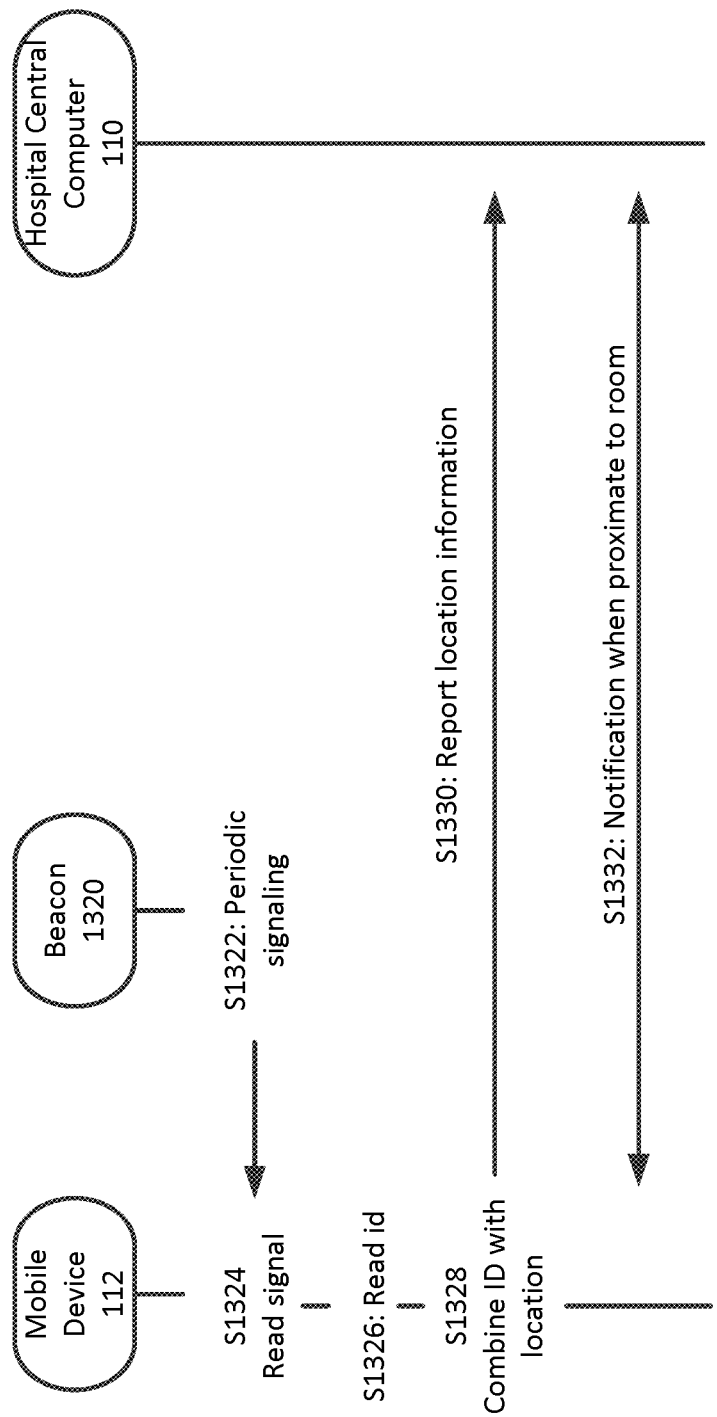
FIGS. 13A, 13B is a sequence diagram for communication between the RFID tag and the scanner or a mobile device and a beacon in accordance with an exemplary aspect of the disclosure.
Figure 13B:
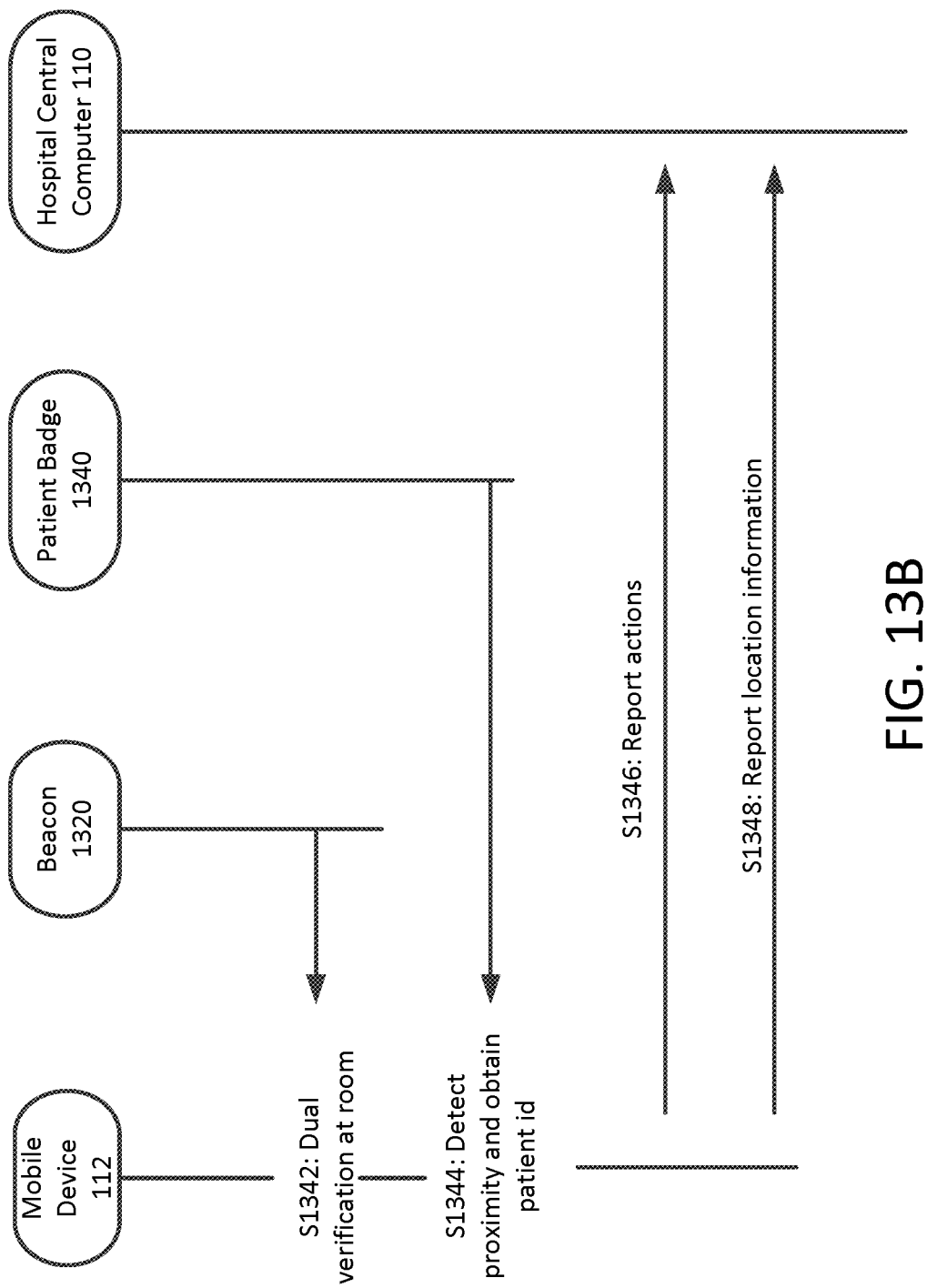

As an alternative to the practitioner ID tag, a mobile device 112, in possession of a healthcare provider, equipped with Bluetooth Low Energy (BLE) and Near Field Communication (NFC) together with a communication system may be used in dual or triple verification of a patient visit by a healthcare provider. The mobile device 112 may also be used to track a healthcare provider's location. FIGS. 13A, 13B is a sequence diagram for communication between the mobile device 112 and a beacon, to monitor location of the healthcare provider, and between the mobile device 112 and a patient badge, to verify the location as proximate to the particular patient.

The mobile device 112 may contain a BLE detector 818. Beacons 1320 may be deployed throughout the hospital so that the location of the mobile device 112 can be monitored. The mobile device 112 may be associated with the ID of the healthcare provider by way of authentication of the healthcare provider with the mobile device 112. The authentication of the healthcare provider may be performed by conventional methods, such as a user name and password, or two factor authentication, or other authentication methods, such as fingerprint or voice print. Provided the authentication, the location of the mobile device 112 will constitute a location of the healthcare provider. Beacons 1020 may be configured as a BLE transmitter to, in S1322, transmit a periodic signal from the fixed position of the beacon 1320. The mobile device 112, in S1324, can detect a transmitted BLE signal by BLE detector 818 and, in S1326, will collect the ID and location of the beacon 1320. In S1328, the location data in combination with the ID, and, in S1330, is forwarded to the hospital central computer 110 to determine the mobile device's location. The communication between the mobile device 112 and the hospital central computer 110 may be performed using WiFi.

The position of the beacon 1320 may be at the entrance to a patient room, and in that case, in S1332, the mobile device's location may be determined by the hospital central computer 110 as being the entrance to the patient room. In one embodiment, the mobile device 112 will be provided with a geographic map that indicates the location of the mobile device.

In S1342, the mobile device 112 may perform a dual verification that the healthcare provider is located at a particular patient room. The mobile device 112 can detect the transmitted BLE signal and will collect the id and location of the beacon 1320. In addition, the mobile device 112 can be configured to detect distance and orientation such that the mobile device 112 is required to be placed at a specific orientation and distance relative to the beacon 1320, then moved to a second orientation and distance in a certain path, as a second verification that the mobile device 112 is located at the patient room. The movement and orientation may be detected using an accelerometer. The distance relative to the beacon 1320 may be determined based on the strength of the BLE signal. The first verification including the location and id of the beacon 1320 may indicate a temporary location of the mobile device 112 as it passes by the beacon 1320. Upon completion of the second verification, the ID of the healthcare provider, the patient room that the mobile device is located may be automatically transmitted to the hospital central computer 110.

The mobile application 904 may be configured to record a time to mark beginning of care for a patient when the mobile application 904 detects the predetermined movement gesture and the predetermined distance range and creates a link between the ID data and the patient's electronic medical record.

A patient may be provided with a patient badge that stores identification information of the patient. Reading identification information of the patient may be used to verify a location as proximate to the particular patient. In S1344, the mobile device 112 may be configured to function as a near field communication (NFC) device and can read the identification information of the patient from the patient id badge. The mobile application 904 may be configured to automatically transmit the patient identification information to the central computer 110 to be related to the ID of the healthcare provider.

In S1346, the mobile application 904 may display a user interface for inputting a report of actions taken with the patient, such as a list of checkboxes for actions that may be taken.

At a period of time after beginning of a patient visitation, the mobile device 112 may detect that it is being moved out of the patient room. In S1348, the mobile device 112 may transmit a message to the hospital central computer 110 that includes time and location of the mobile device 112.

Figure 14:
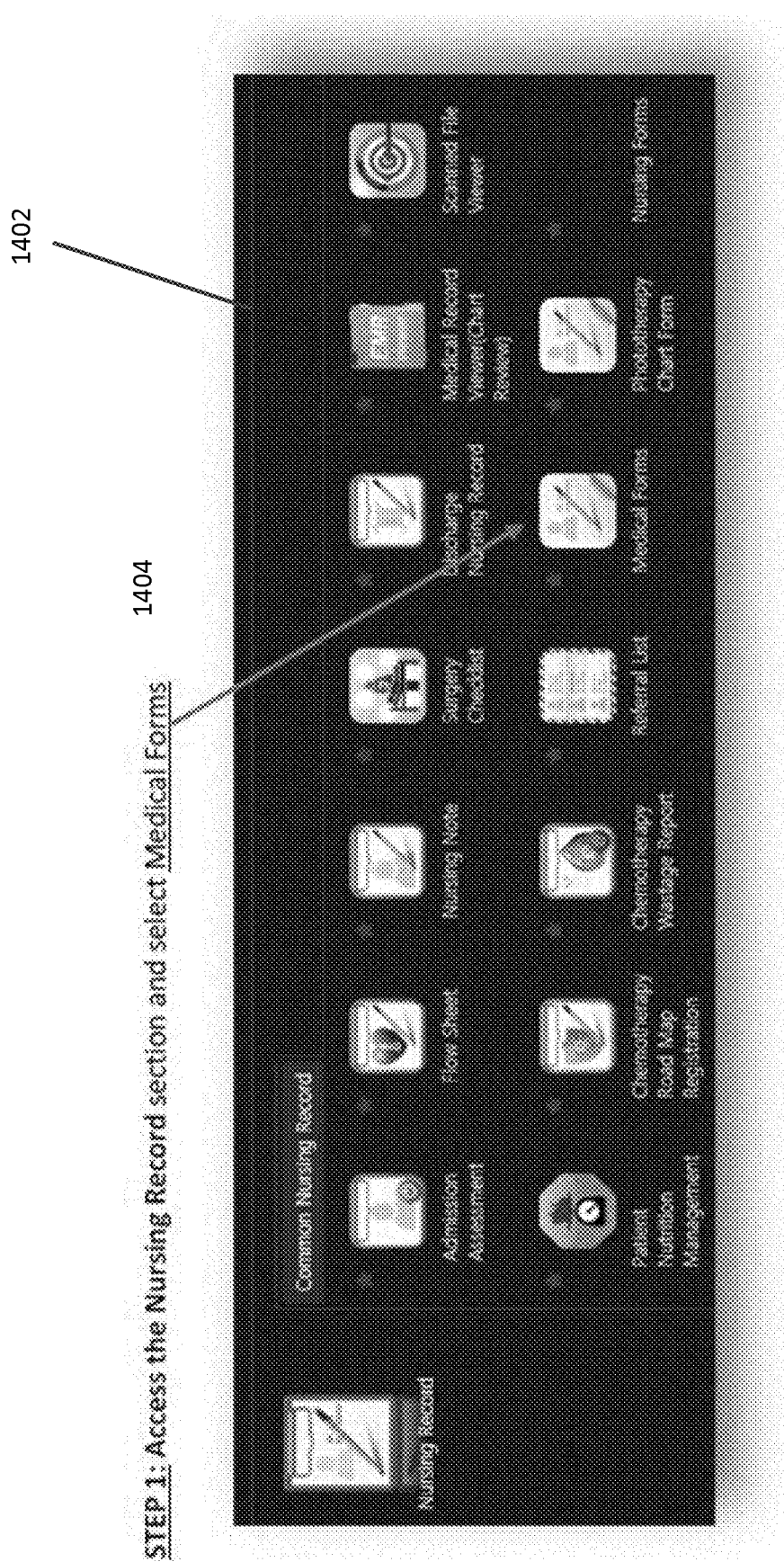
FIG. 14 is an exemplary screen for a step in the patient risk assessment in accordance with an exemplary aspect of the disclosure.

FIG. 14 illustrates an exemplary screen for accessing the nursing record section of a hospital care system. The nursing record 1402 may be a component in the central computer system 110. A primary nurse 302 may select an icon 1404, among icons in the nursing record 1402, that brings up medical forms.

Figure 15:
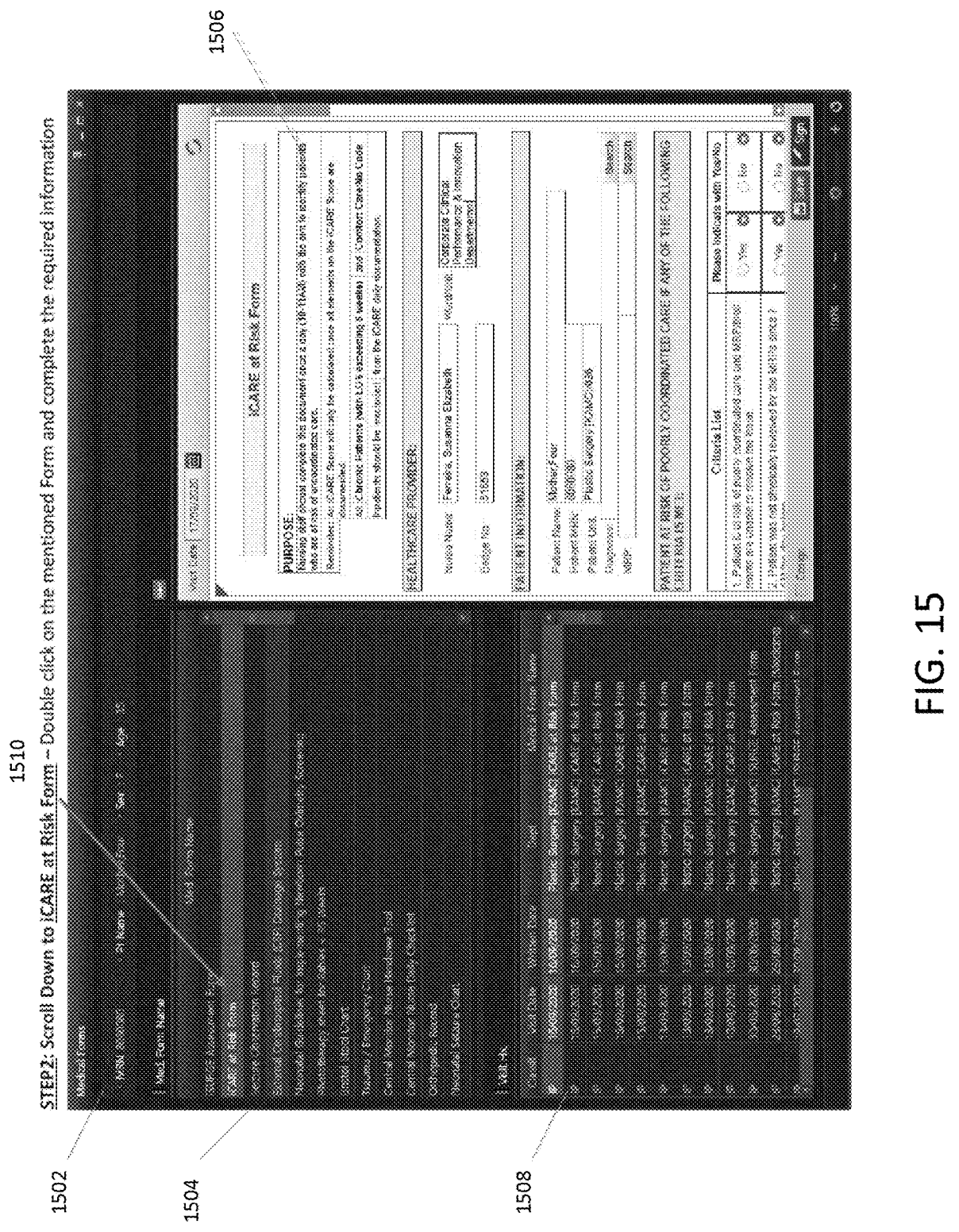

FIG. 15 illustrates an exemplary screen that may be displayed as a result of selecting the medical forms icon 1304. The exemplary screen 1502 may display a list of medical forms 1504. In the screen 1502 of FIG. 15, a primary nurse 302 may select a risk assessment form 1510 from among listed forms 1504. The risk assessment form 1510 may be a form that is specific to a department (medical ward) that is associated with a particular patient. When the risk assessment form 1510 is selected, the exemplary screen 1502 may display a history of risk assessment forms 1508 associated with a patient. The exemplary screen 1502 may display a risk assessment form 1506 that may be filled in next. FIGS. 16 to 21 illustrate particular sections of the risk assessment form 1506.

FIG. 16 illustrates a section of the risk assessment form containing fields for entering information about the healthcare provider. In S706, the healthcare provider information may be populated. A healthcare provider section 1602 includes fields that may be populated with healthcare provider information associated with the healthcare provider id when the healthcare provider id tag is scanned, S1002. The fields may include a field 1604 for the name of the healthcare provider, a field 1608 for the ward that the healthcare provider is part of, and a field 1606 for a badge id number for the healthcare provider.

FIG. 17 illustrates a section of the risk assessment form containing fields for entering information about a patient. Some of the fields for the patient information may be populated based on information provided when the patient is first assigned to a patient room. The patient unit field 1708, for example, will be populated based on the department that a patient is assigned upon admission to the hospital. Likewise, the patient name field 1704 and patient medical registration number 1706 may be populated with information of the patient obtained when the patient is admitted to the hospital. The patient name, medical registration number and patient unit may be populated by way of a terminal 102 located in the patient hospital room.

Remaining patient information including in S708, a diagnosis field 1710 and responsible physician field 1712 may be entered by a primary nurse 302 during the period 502 of filling out the risk assessment form. In one embodiment, the diagnosis field 1710 may be filled in based on information that has been completed by a responsible physician 312 during an initial consultation with the patient. The initial consultation with the responsible physician 312 may take place during admission to the hospital, or at some period before the patient is assigned to a department. In some situations, a patient may be admitted to the hospital and transferred to a room for initial consultation for purposes of examining the patient and determining an appropriate department that the patient may be assigned. The responsible physician 312 may enter a diagnosis into the patient's electronic medical record at the time of the initial consultation, or may enter the diagnosis at a later time. The primary nurse 302 may populate the diagnosis field 1710 by performing a search function (pressing a search button) and selecting a diagnosis term 1720 to be used to populate the field. In a similar manner, in S710, the patient's responsible physician field 1712 may be populated by performing a search function (1730) to search among physicians based on the responsible physician's name, badge number, or department in order to obtain the information 1732 for the responsible physician.

FIG. 18 illustrates an exemplary risk assessment questions section to assess poorly coordinated care for a particular hospital department. The questions section 1802 may be a list of checkboxes that may easily be reviewed and checked by a primary nurse 302. In S712, the primary nurse 302 may address the questions based on a consultation with the patient, and a physical and visual examination of the patient during the time period 502. The questions may be related to potential concerns about a compromise to the coordination of care that the primary nurse may observe during the consultation and visual examination. Some questions may relate to concerns that a patient may express during the consultation with the primary nurse 302. For example, the patient may express a concern that the medical condition appears to be getting worse, that there may be symptoms that come to mind after the initial consultation with the responsible physician, or other issues that may reflect a concern as to whether the treatment is sufficient or should be more aggressive, or may have been misdiagnosed.

In S716, the questions section 1802 requires that all questions to be addressed in order for a risk score to be generated in S718. In some embodiments, a question section 1802 must be completed before the risk assessment will allow the primary nurse 302 to move on to a next screen, or log out of the risk assessment. In one embodiment, if a Yes or No checkbox is not selected, an automated risk score will be generated by default.

In S714, some questions may involve sub-questions in order to fully answer the question. Some questions may require further explanation.

Figures 19, 20:
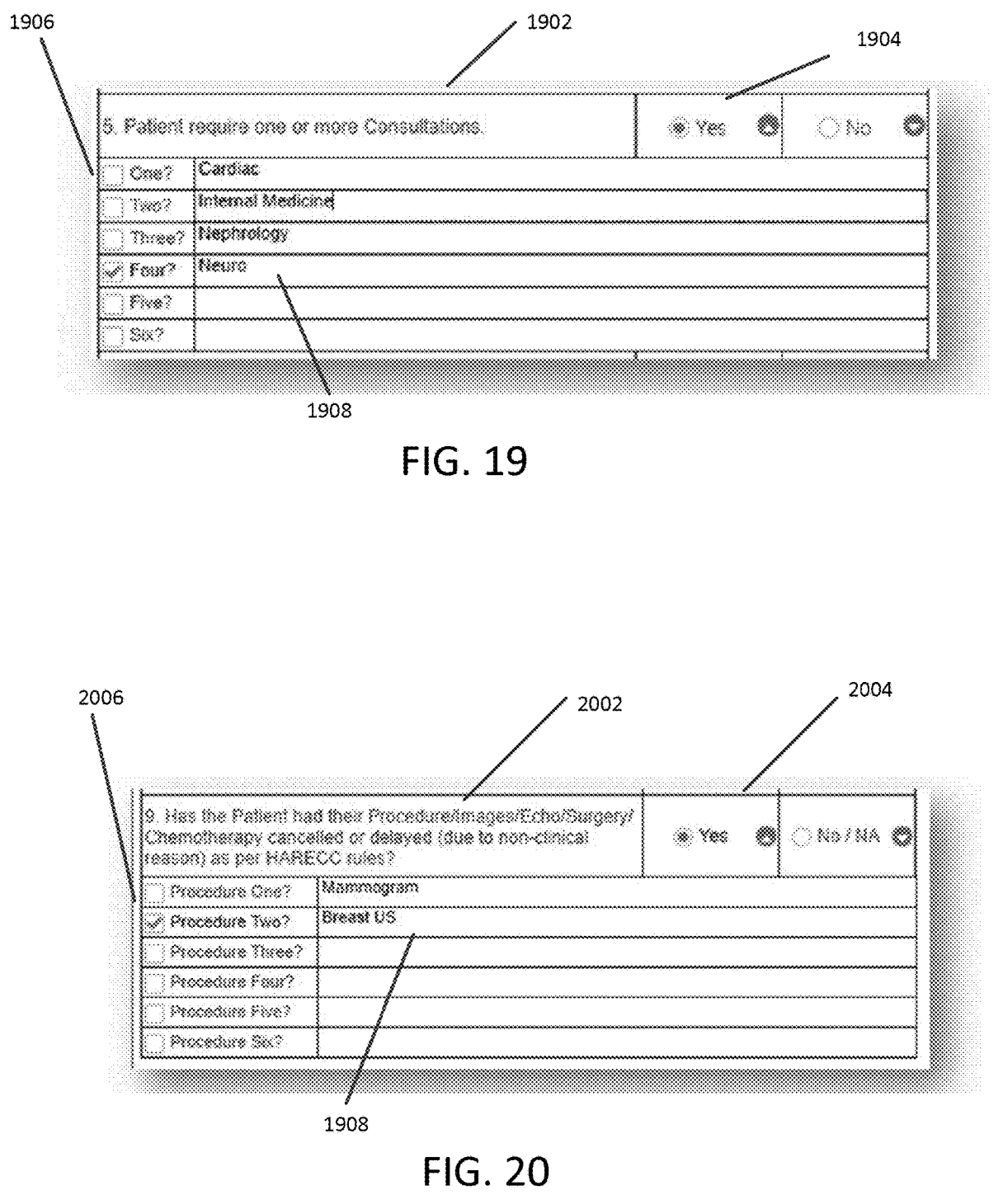

FIG. 19 illustrates an exemplary sub-question for a risk criteria that requires further explanation. Some questions may best be answered with a quantitative value that may change based on visits with a patient. Regarding FIG. 19, an issue regarding coordination of care may be that a patient requires one of more consultations. The risk assessment form may include one or more fields into which the type of consultation may be entered for each consultation. In one embodiment, when a response to a quantitative question is "YES," the form may expand into a list of checkboxes to aid in selection of a quantity and an associated explanation or description related to the quantity. In the case that there is a sequence of quantities, each quantity up to the present quantity may be accompanied by an explanation or description. In some embodiments, a greater quantity may contribute to a higher risk score. A risk score may change each time a primary nurse 302 completes a risk assessment form.

In the example illustrated in FIG. 19, the question 1902 is whether a patient has had one or more consultations, in some cases with different responsible physicians 312 or healthcare givers/consultants in different departments. When the checkbox "YES" 1904 is checked, the question will expand to a list of checkboxes 1906. The current consultation will be indicated by a check in the checkbox 1908. In the example shown in FIG. 19, it can be seen that this particular patient may have had consultations with different departments, possibly indicating concerns or difficulty in determining a medical condition for this patient.

FIG. 20 illustrates an exemplary sub-question for a risk criteria that requires further explanation. A question concerning a cancelation or delay of one or more procedures 2002 may raise an issue related to poor coordination of care. The example question 2002 may concern whether a procedure or procedures has been delayed or canceled due to non-clinical reasons. When the checkbox "YES" 2004 is checked, the question will expand to a list of checkboxes 2006. A sequence of checkboxes may show a history of procedures that have been canceled or are being delayed. The current procedure that is being delayed or canceled may be indicated by a check in a checkbox 2008. The number of procedures that have been delayed or canceled may contribute to a higher risk score. It can be seen that this particular patient may have had miscommunication of diagnosis or miscommunication in a medical condition that caused a procedure to be delayed or canceled.

Figure 21:
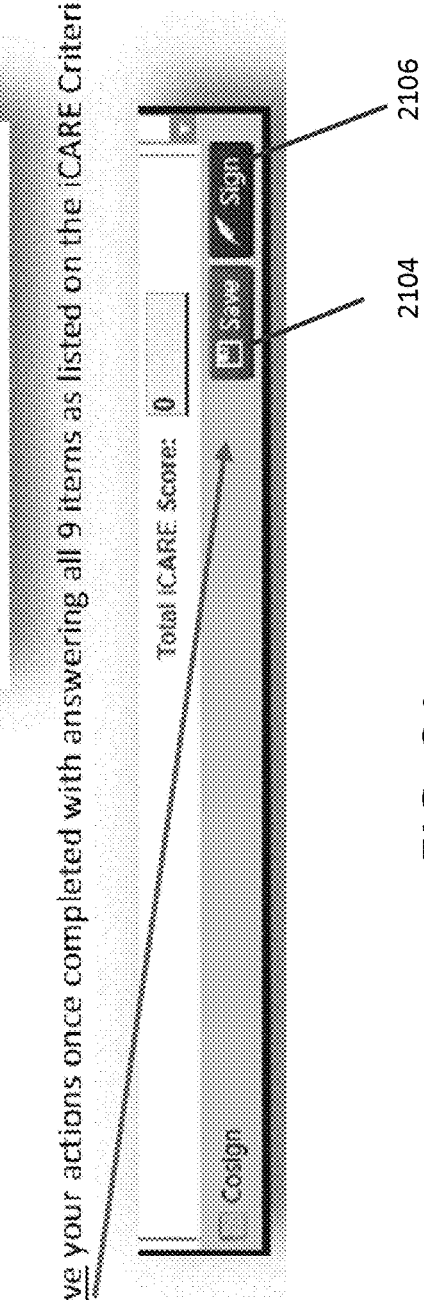
FIG. 21 illustrates a section of the risk assessment form that displays a risk score that is calculated based on the answers to the questions in the risk assessment form.

FIG. 21 illustrates a section of the risk assessment form that displays a risk score that is calculated based on the answers to the questions in the risk assessment form. In S718, a risk score may be determined based on values selected in the risk assessment form that is completed on daily basis for each hospital stay day to reflect the risk of poorly coordinated care as the patient's condition or clinical needs change over time. When none of questions in the risk assessment form are applicable for a patient, a default risk score of zero will be displayed in the form. In some embodiments, the primary nurse 302 that completed the risk assessment form will be required to save the completed form by activating a save function 2104. In some embodiments, the primary nurse 302 that completed the risk assessment form will be required to sign the completed form and associated risk score.by activating the sign function 2106. The saved form may be stored in a database in the central computer system 110.

Risk assessment forms are to be completed for all patients before the end of period 502. Within a predetermined time period, the charge nurse will review the risk assessment screen of their unit, for any patient without a score, charge nurse will review the patient electronic medical record with the patient's primary nurse and review the patient's eligibility for form completion and ensure form completion for all eligible patients.

Figure 22:
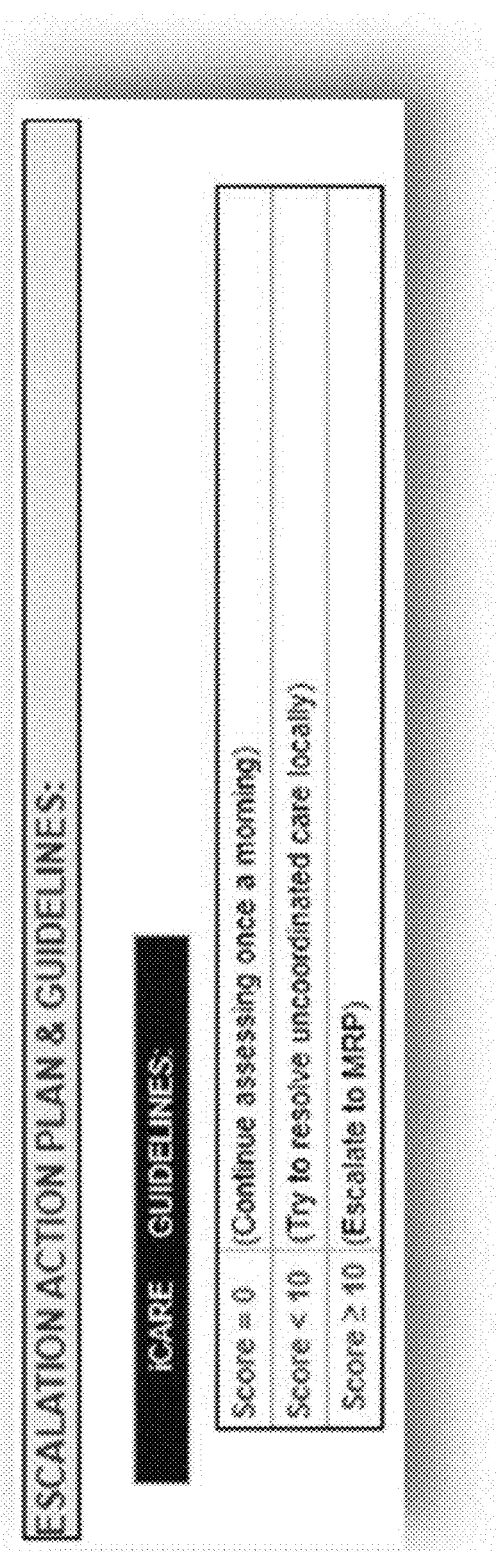
FIG. 22 is a set of escalation guidelines in accordance with an exemplary aspect of the disclosure.

In S720, in period 504, the charge nurse 304 will be provided with a display of risk scores for all patients in their department (ward). The charge nurse 304 may verify scores by reviewing the risk assessment form associated with the particular patient. According to an escalation guideline, as in FIG. 22, in S722, a risk score of zero may lead to an action that the risk assessment will be performed the next day. According to the escalation guideline, in S724, a risk score that is greater than zero but less than a predetermined threshold, for example a risk score threshold of 10, will be resolved locally, in S726, by the primary nurse 302 and charge nurse 304. Only those patients having a risk score of greater than the predetermined threshold may be subject to, in S728, an escalation process.

In S728, the escalation process involves communication based on the escalation communication protocol.

FIG. 23 is an exemplary list of healthcare provider to be communicated with in the case of an escalation process. In one embodiment, unresolved risk issues may be communicated using a video conference system or via e-mail. In the embodiment, a risk assessment support team may be designated as preferred points of contact for resolving risk issues related to poorly coordinated care.

Figure 24:
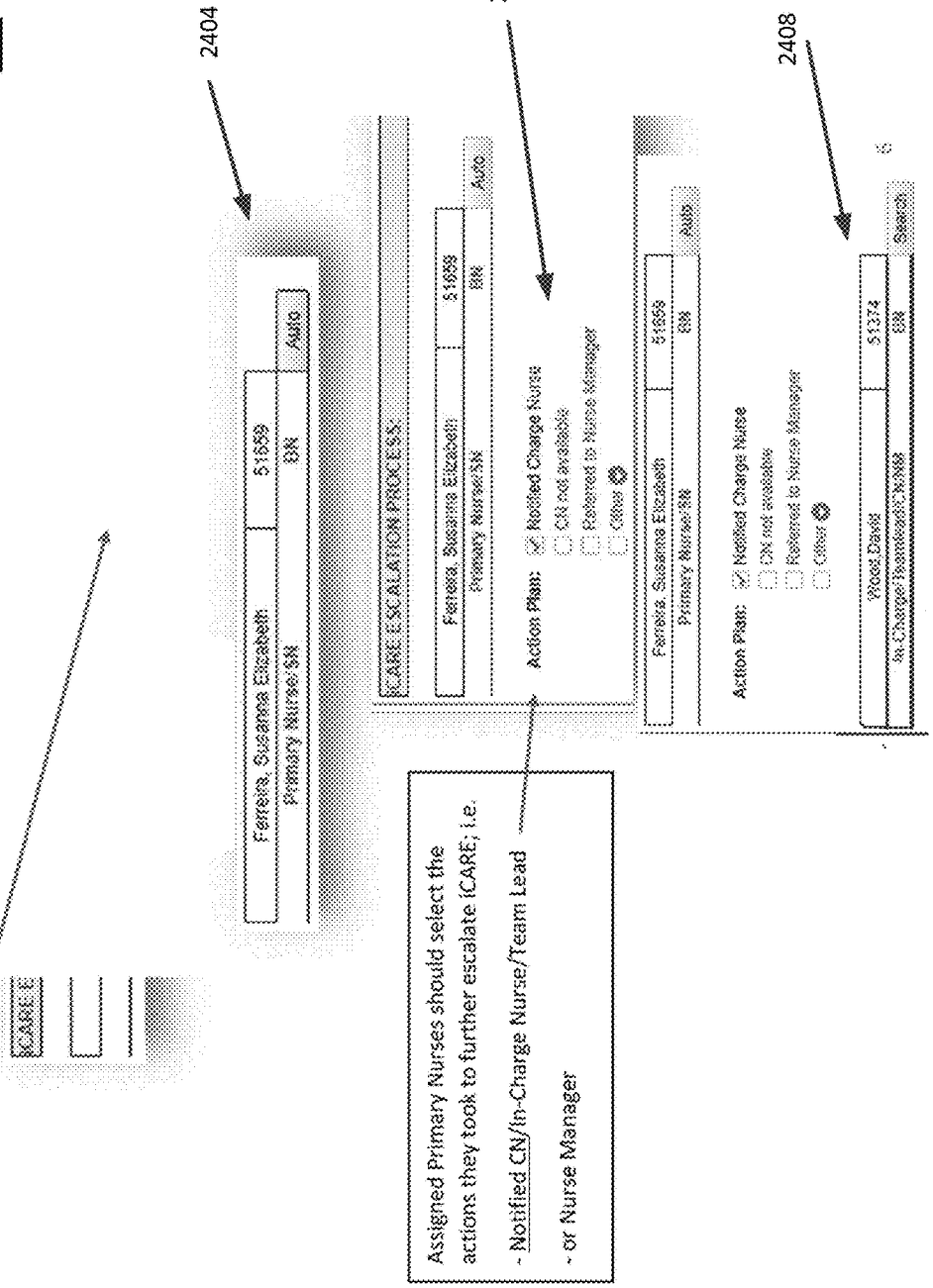
FIG. 24 illustrates an exemplary documentation of an escalation process in accordance with an exemplary aspect of the disclosure.

FIG. 24 illustrates an exemplary documentation of an escalation process in accordance with an exemplary aspect of the disclosure. In 5730, an escalation process may be initiated with a primary nurse 302 assigned to the patient. The identifying information of the primary nurse may be captured using the id tag of the primary nurse or by scanning the mobile application icon 906, as discussed above. An escalation process form 2402 may be automatically populated with the primary nurse's identification information 2404. The escalation process form 2402 may include checkboxes 2406 for actions taken to escalate risk issues. In the example shown in FIG. 24, the action checkboxes 2406 include actions of notified the charge nurse, charge nurse is unavailable, referred to the nurse manager. Other actions taken may be entered by the primary nurse.

When the primary nurse takes an action to notify a charge nurse of nurse manager, the information of the charge nurse or nurse manager is populated in fields 2408. FIG. 25 is a step of co-signing by a charge nurse or nurse manager. In one embodiment, the charge nurse or nurse manager are required to enter credentials as a verification of the escalation process initiated by the primary nurse. Once the credentials of the charge nurse or nurse manager have been entered, the primary nurse may save the escalation document 2002 in the central computer system 110.

Figure 26:
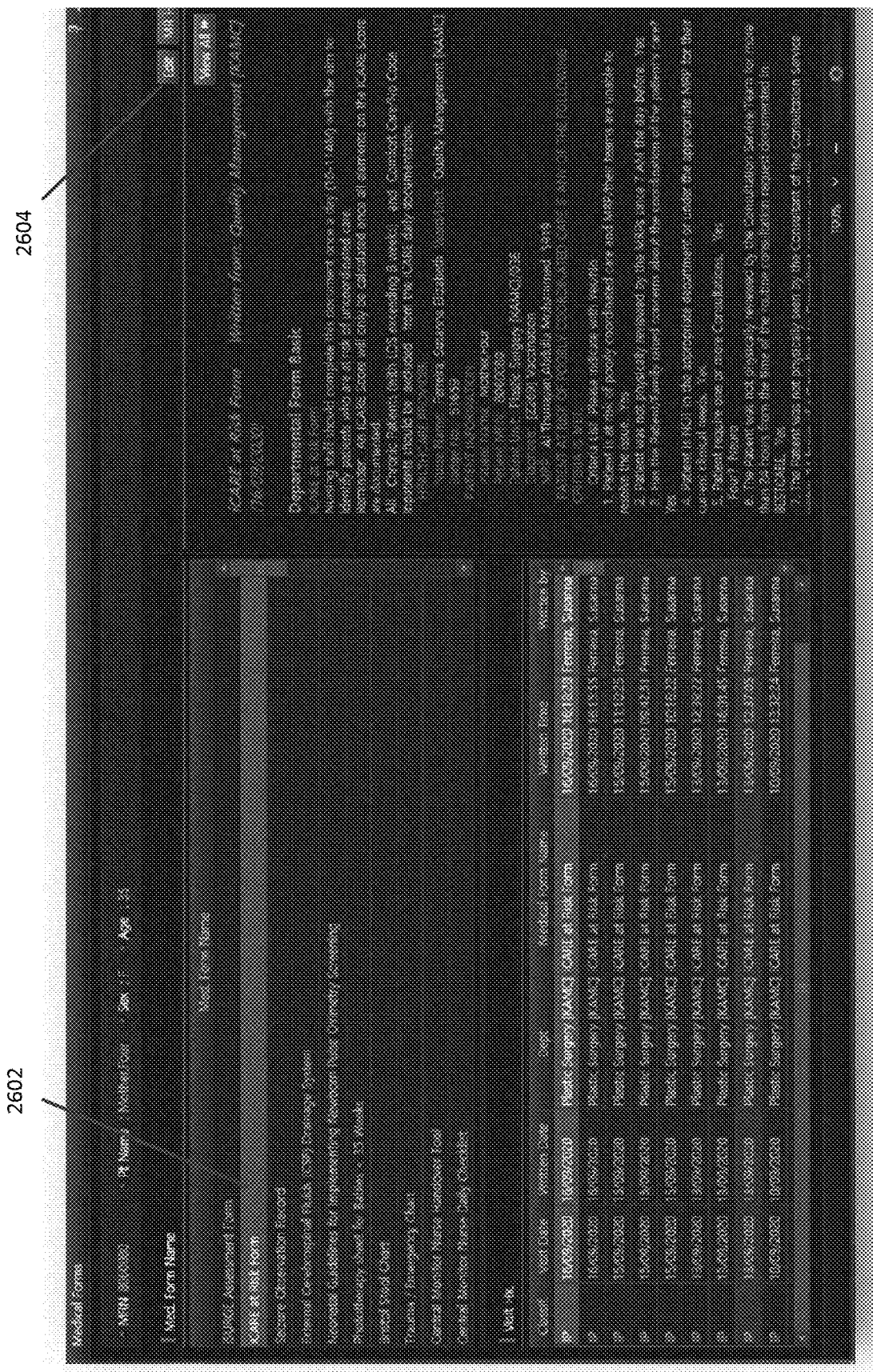
FIG. 26 illustrates steps for the charge nurse or nurse manager to begin revising the risk assessment form for a patient as issues are resolved.

FIG. 26 illustrates steps for the charge nurse or nurse manager to begin revising the risk assessment form for a patient as issues are resolved. In S732, actions taken to resolve risk issues may be performed based on a timer, for example, in the mobile device 112. Any issues that remain unresolved by the end of a predetermined time period may automatically be subject to an escalation process. The most current risk assessment form for a patient may be accessed by selecting the form 2602 from a list of forms by the charge nurse or nurse manager. A set of edit operations may be enabled upon selection of an EDIT button 2604.

FIG. 27 illustrates a portion of an edited version of the risk assessment form. In S734, the edited version 2702 contains a list of checkboxes 2706 that upon being checked show actions that the charge nurse or nurse manager took in an attempt to resolve any uncoordinated care issues. The edited version 2702 may be populated with identification information 2704 of the charge nurse or nurse manager. The list of checkboxes, as shown in the example in FIG. 27, may include actions of reviewed the patient's medical plan, escalated to the nurse manager, escalated issues to the responsible physician, escalated to department chairmen, issues remain unresolved and escalated to CCPID. Other actions taken, not listed, may be entered by the charge nurse.

Figure 28:
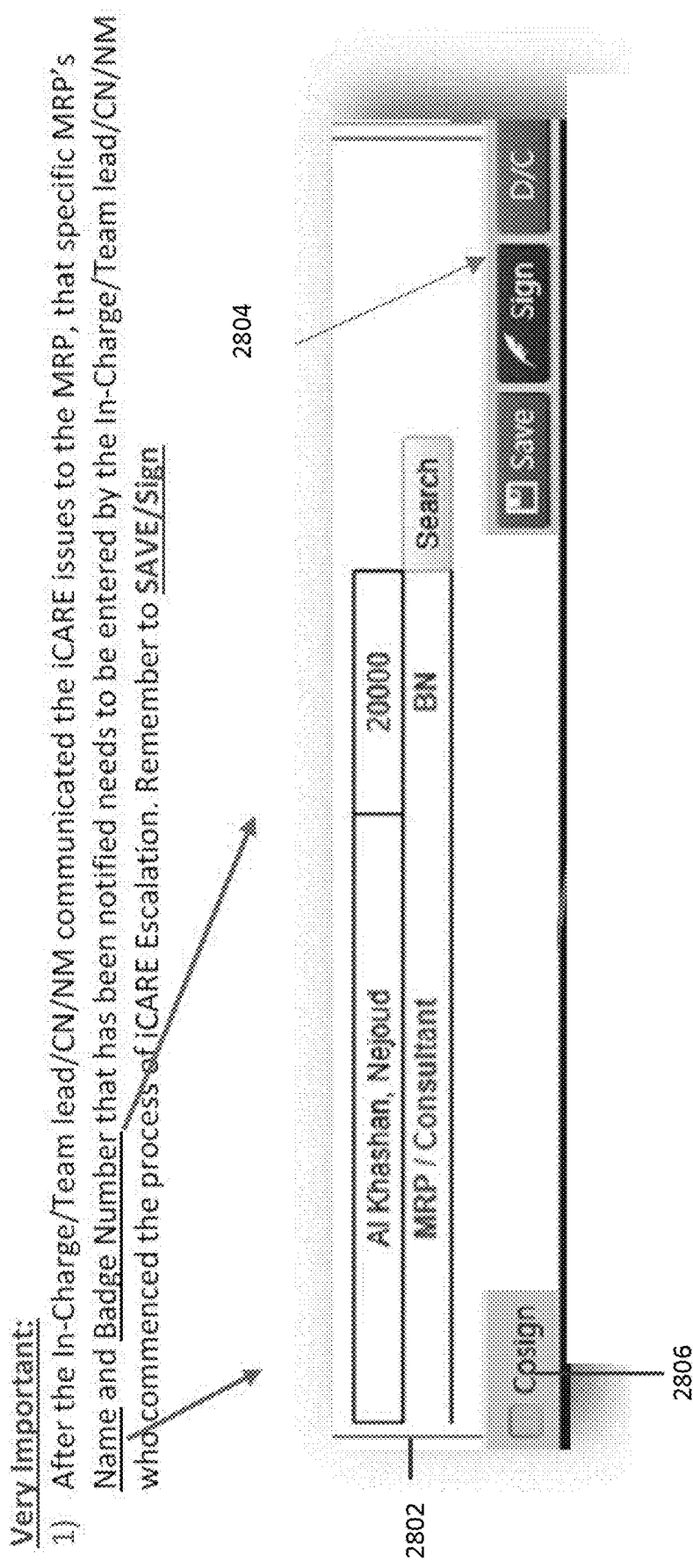
FIG. 28 illustrates a case in which the action taken is that unresolved issues are escalated to the responsible physician.

FIG. 28 illustrates a case in which the action taken is that unresolved issues are escalated to the responsible physician.

In S740, a message, for example in the form of an e-mail, will be sent to the responsible physician. The charge nurse or managing nurse enters the identification information 2802 for the responsible physician that has been notified. The charge nurse or managing nurse will save using a save button 2804 the responsible physician information to the central computer system 110.

Figure 29:
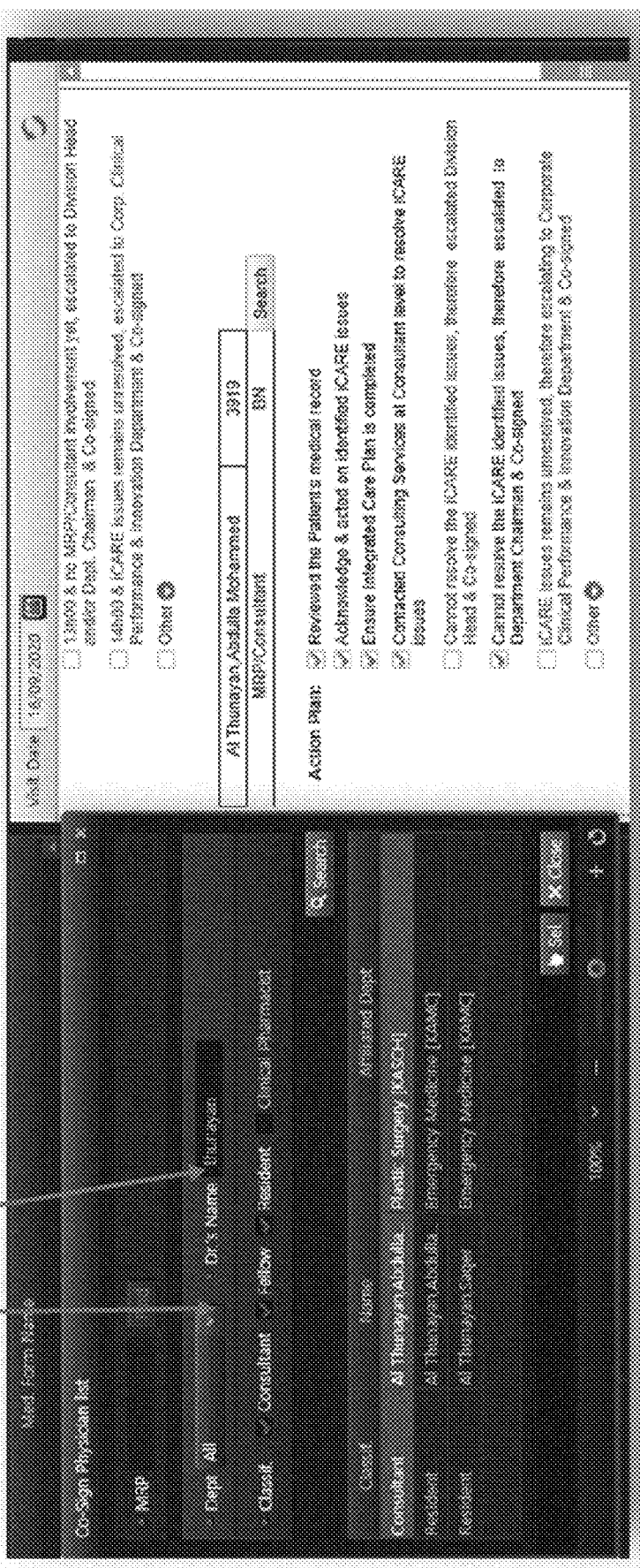
FIG. 29 illustrates entry of responsible physician information in order to obtain a cosign physician list.
Figure 30:
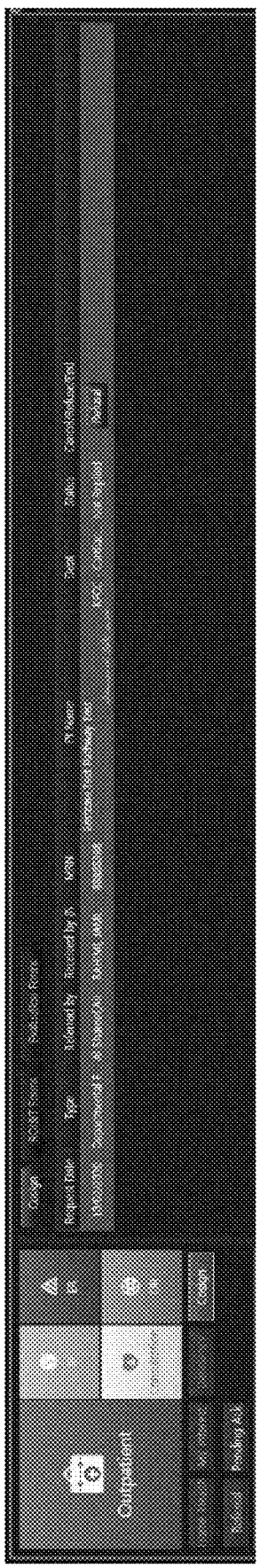
FIG. 30 illustrates a cosign options screen for a charge nurse.

In one embodiment, the responsible physician that has been notified of the unresolved issues is required to cosign the entry of identifying information. The requirement to cosign may be displayed as an indication 2806 in the identification entry section. Upon completion of entry of responsible physician information, a cosign physician list will be provided, as shown for example in FIG. 29. The co-sign physician list may be a drop down list 2904 of physician names for a department 2902. Upon selection of the responsible physician from the drop down list, an automated push notification will be sent to the selected responsible physician in their cosign options screen. An example of a cosign options screen for a charge nurse is shown in FIG. 30.

FIG. 31 illustrates a risk assessment registry that contains a record of all patients that have been subject to a risk assessment. The risk assessment registry 3102 may document patients that have a risk score above a predetermined risk score threshold, such as 10, and may include a record of the cumulative risk score 3104. In one embodiment, the risk assessment registry 3102 may summarize the escalation path 3102 that had been used. The risk assessment registry 3102 may document the risks identified 3108 and the actions taken 3110 to resolve the risks.

FIG. 32 illustrates options 3202 that the responsible physician will be provided once notified of a request for cosign. In S742, the responsible physician may be presented with a list of cosign items 3212 upon logging into their interface and selecting a Cosign button 3204.

Figure 33:
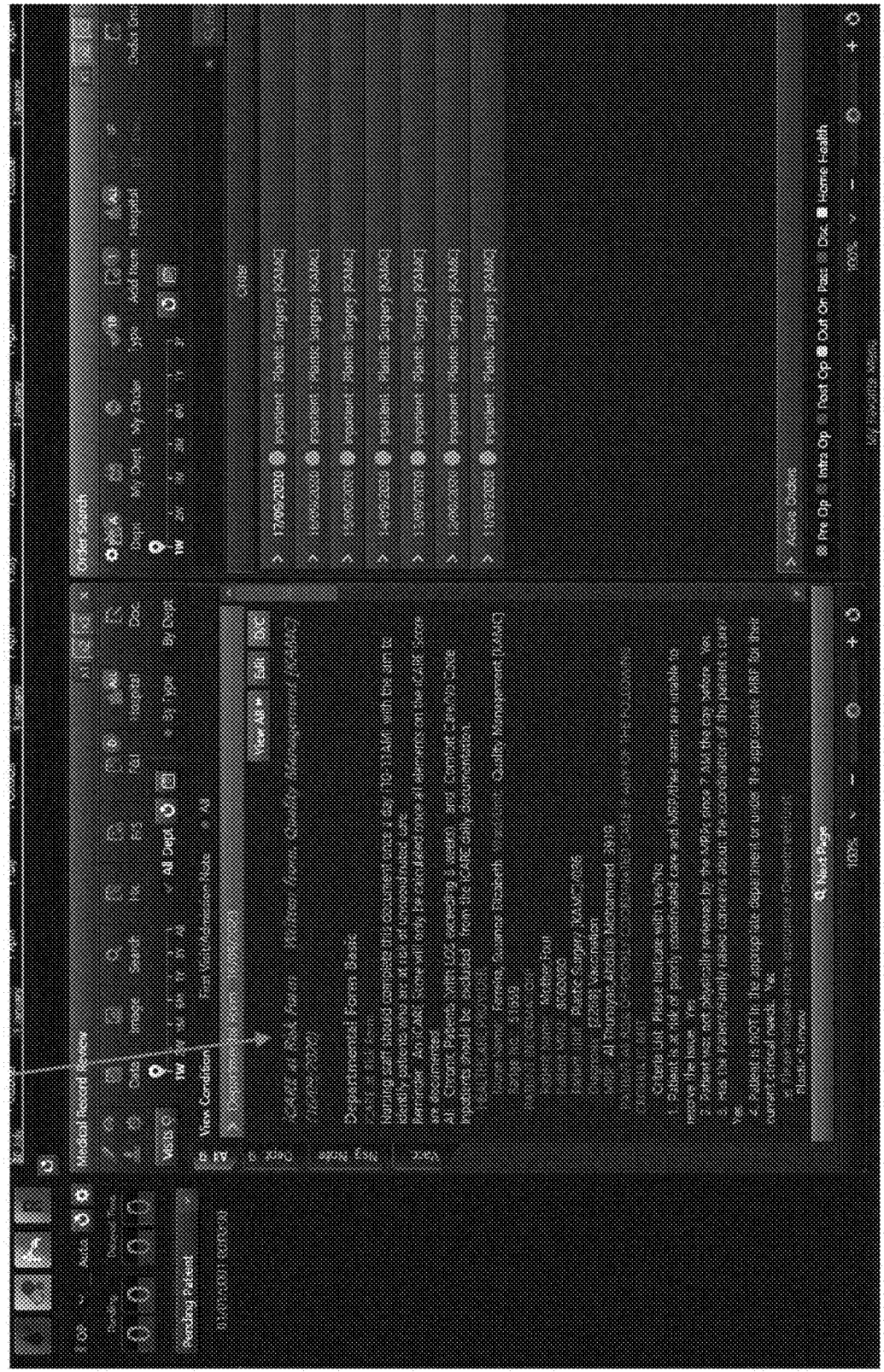
FIG. 33 illustrates an example screen that includes the risk assessment form.

In S744, when a responsible physician selects an item for cosign 3214, the risk assessment form will automatically open for the department with regard to the patient associated with the risk assessment. FIG. 33 illustrates an example screen that includes the risk assessment form 3302.

The responsible physician may be faced with situations in which there are conflicts between patients that need to be resolved in a limited time period. In S746, a decision is made as to whether there is a potential conflict between patients. In S758, the central computer system 110 may perform an analysis in order to resolve cases in which there are conflicts between patients. For example, there may be an unusually large number of patients having high risk assessment scores such that a responsible physician may not be able to address all risk assessment issues in the designated time period. In some cases the high level risk score or criteria list may require further explanation in order to obtain a better understanding of the issue and possible solutions.

As one example, a risk criteria for a patient may indicate that the patient has had several consultations with physicians from various departments. Such a case may be an indication that the patient has multiple medical conditions that need to be addressed, or may be an indication that the patient's condition is difficult to determine or may be quickly changing and becoming more severe.

The present responsible physician may need further explanation in order to determine the reason for the various consultations. This case may be reflected by a risk assessment score that is determined not just on the number of consultations, but also on the types of consultations. The high risk assessment score may be given high priority so that the responsible physician may spend some time performing further research on the reason for the high score.

In one embodiment, the risk assessment score may be determined based on a decision tree. Also, one approach may be a decision tree in which the risk assessment score is a category, rather than a numerical value. For example, the risk assessment score may be one of several qualitative values, such as no risk, medium risk, and high risk. Patients that have a risk score of medium risk may be subject to resolution locally, while patients that have a risk score of high risk may require escalation.

A risk assessment score decision tree may be learned over time. For example, one of several known inductive learning algorithms may be applied that takes as input training examples, and produces a classification-type decision tree. Training examples may be based on a history of past patient risk assessment scores and the associated conditions that lead to those scores (see for example conditions in FIGS. 18-20). In one embodiment, the completed risk assessment form and associated score may be stored in a database in the central computer system 110. Values of the risk assessment form and resulting scores may be used as training examples for a classification-type decision tree.

Alternatively, the decision tree may be used to determine actions that a responsible physician should take based on risks that are identified. In one embodiment, the data logged into the registry, as shown for example in FIG. 31, may be used to create a decision tree for deciding recommended actions. In one embodiment, a decision tree may include:

If the risk assessment is high risk and the primary nurse 302 indicates that the patient is not in an appropriate department for current medical needs, the central computer system 110 automatically escalates to the responsible physician 312 to visit the patient and further evaluate an appropriate department for the patient. If the risk assessment is high and the primary nurse 302 indicates that the patient is not being evaluated by an appropriate responsible physician 312 for the current clinical needs, the central computer system 110 automatically escalates to a department chairmen 314 to evaluate an appropriate responsible physician 312 for the current clinical needs.

As the amount of data stored in the registry becomes large, the data may be used by a recommendation engine in order to provide recommended actions based on similar risk assessments.

Figure 34:
FIG. 34 illustrates a section of a screen that is automatically opened.

FIG. 34 illustrates a section 3402 of a screen that is automatically opened. In S748, the responsible physician may choose to edit (edit button 3404) the risk assessment form in order to document any actions taken for the unresolved issues. At this time a scan process as in FIG. 10 may commence. The responsible physician will be given a certain period of time to solve identified risk assessment issues.

FIG. 35 illustrates a portion 3502 of an interface for a responsible physician that includes a list of checkboxes 3504 for actions that the responsible physician may choose to take in order to resolve the patient's unresolved risk assessment issues. In S750, the responsible physician may review the list and select actions that will be performed (by clicking on an associated checkbox). Among the actions that a responsible physician may take to resolve the patient's issues may include review the patient's medical record, acknowledge and act on identified issues, ensure an integrated care plan is completed, contact consulting services to resolve issues, could not resolve the identified issues, and escalate to either a division chairman, a department chairman, or CCPID.

Figure 36:
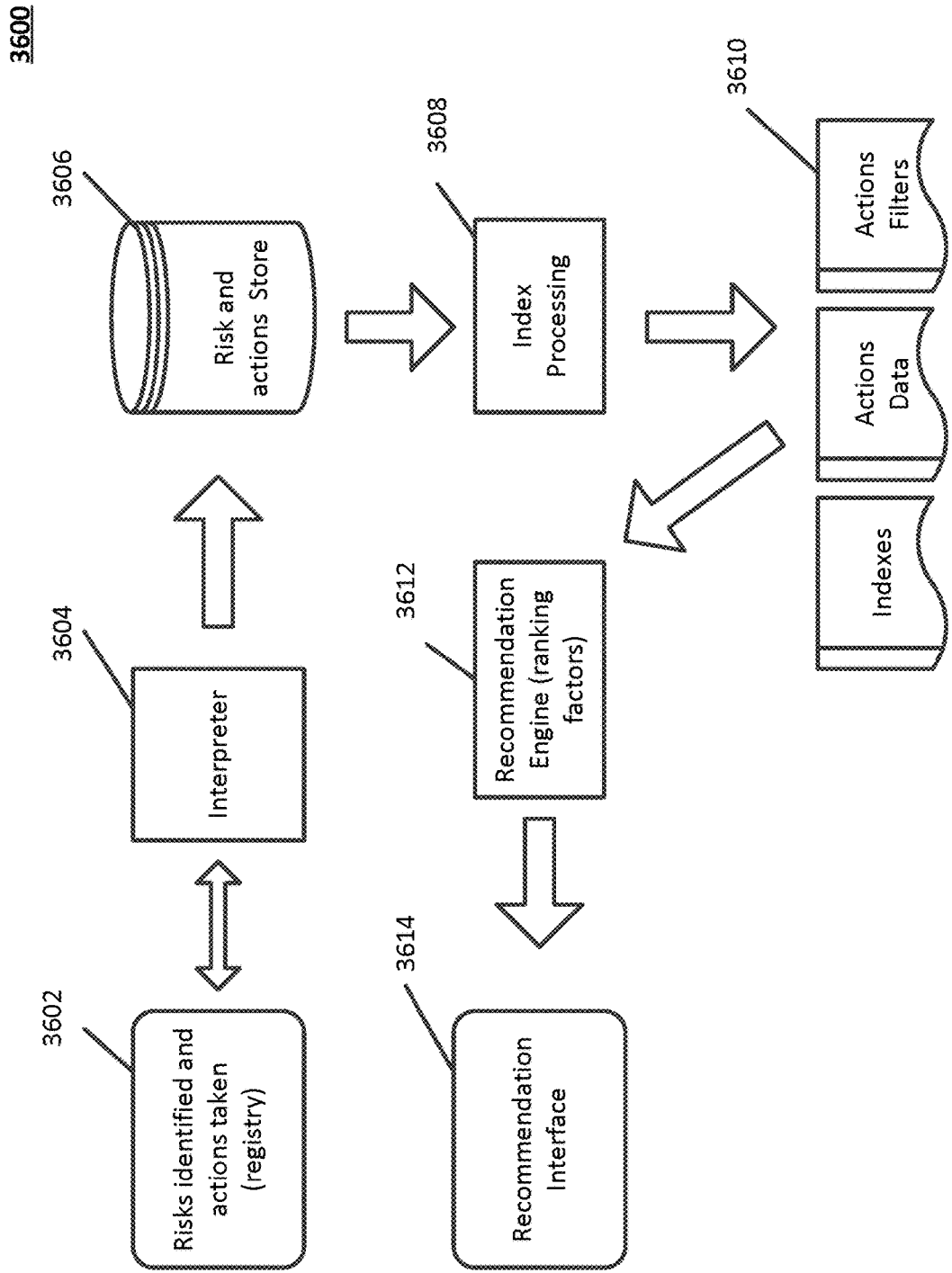
FIG. 36 is a diagram for a recommender system in accordance with an exemplary aspect of the disclosure.

FIG. 36 is a diagram for a recommender system. The recommender system 3600 may be used for providing actions to resolve a risk identified that are based on similar assessed criteria in risk assessments. The recommender system 3600 works off of an indexed database 3610 of action data and action filters. The indexed database 3610 may be populated with data from a registry (see FIG. 31) stored in a database in the central computer 110. The recommender system 3600 may include an interpreter 3604 that extracts data from the registry and stores a relationship of risk and actions in a database 3606. Data in the risk and actions database 3606 may be indexed by an index processing operation 3608 and the indexed data is stored in the indexed database 3610.

The recommender system 3600 includes a recommendation engine 3612 that retrieves and ranks recommendations. In the case of actions for a particular risk identified, a recommendation may be for the risk identified in a risk assessment form. In some embodiments, the recommendations may be retrieved based on user preferences or typical types of actions. Personal user preferences may be actions that a healthcare provider has entered when the hospital network system 100 is first set up. Typical features may be actions that a healthcare provider would normally take given the risk identified.

In some embodiments, the recommendation engine 3612 may use an action matrix. FIG. 37 illustrates a non-limiting action matrix in accordance with an exemplary aspect of the disclosure. The action matrix in FIG. 37 is a partial matrix showing some example actions for the sake of brevity. Other types of actions may be included in the matrix, including, but not limited to, seen by a healthcare provider, further investigation initiated, consult health services, to name a few. The action matrix may be stored in the central computer system 110 to be compared to a vector of desired features. The desired features may be current user preferences and may take into account the user's current experience level. The recommendation engine 3612 may use one or more similarity metrics and a scoring algorithm to rank recommendations. In an embodiment, the recommendation engine 3612 may generate a set of features that elevate recommendations in order to encourage brevity by changing certain characteristics for an action from those that are recommended. For example, if the recommendation engine 3612 ranks a recommendation high among retrieved recommendations, it may then change one or more characteristics in order to increase a similarity score. Alternatively, the recommendation engine 3612 may change one or more characteristics in a retrieved recommendation, to one up or one down. In one of more embodiments, the recommendation engine 3612 may adjust the action to be more or less precise based on the experience level of the healthcare provider.

The recommendation engine 3607 may output one or more recommendations to a recommendation user interface 3614. The recommendation user interface 3614 may display a list of actions as the recommendations, in which one recommendation may be selected.

FIG. 38 illustrates an exemplary summary of risks identified and whether they have been resolved. An ideal scenario is where the responsible physician has solved all identified risk assessment issues. If all identified issues have been solved within the required time period, the responsible physician needs to document the solution of the issues. The healthcare system will automatically save all risks that have been identified, and will provide a summary 3804 of the solved issues. In one embodiment, the summary of issues 3804 will reflect the questions in the risk assessment form for the patient. In S752, the responsible physician may document whether the identified risks have been solved by selecting "YES" 3408 in the resolved column 3806.

FIG. 39 illustrates a subsequent escalation process in a case where the responsible physician was not able to solve all risk assessment issues within the required time period. In S754, the health care system will perform a decision as to whether issues have been resolved with the time period t1. In S756, if there are still unresolved issues, an escalation pathway will be determined and actions to resolve the unresolved issues will be assessed.

In S760, the responsible physician may enter a consultant to be escalated to. It should be noted that an escalation process may be a lateral escalation where the escalation process is to another responsible physician, such as a responsible physician within another department, being of a different specialty.

Referring to FIG. 39, in the case where the responsible physician was not able to solve at least one risk assessment issue, an interface may be displayed that includes a list of checkboxes 3902 for actions including a checkbox that is selected that, for example, indicates that the responsible physician was not able to resolve an identified issue and that escalation should be to a department chairmen. An e-mail message may be sent to the department chairmen that informs the department chairmen that a risk assessment issue needs to be addressed for a patient. Alternatively, the department chairmen may be contacted by a telephone call, text message, or pager. In S760, the responsible physician will document 3904 the name of the department chairmen that has been contacted for the escalation pathway.

Figure 40:
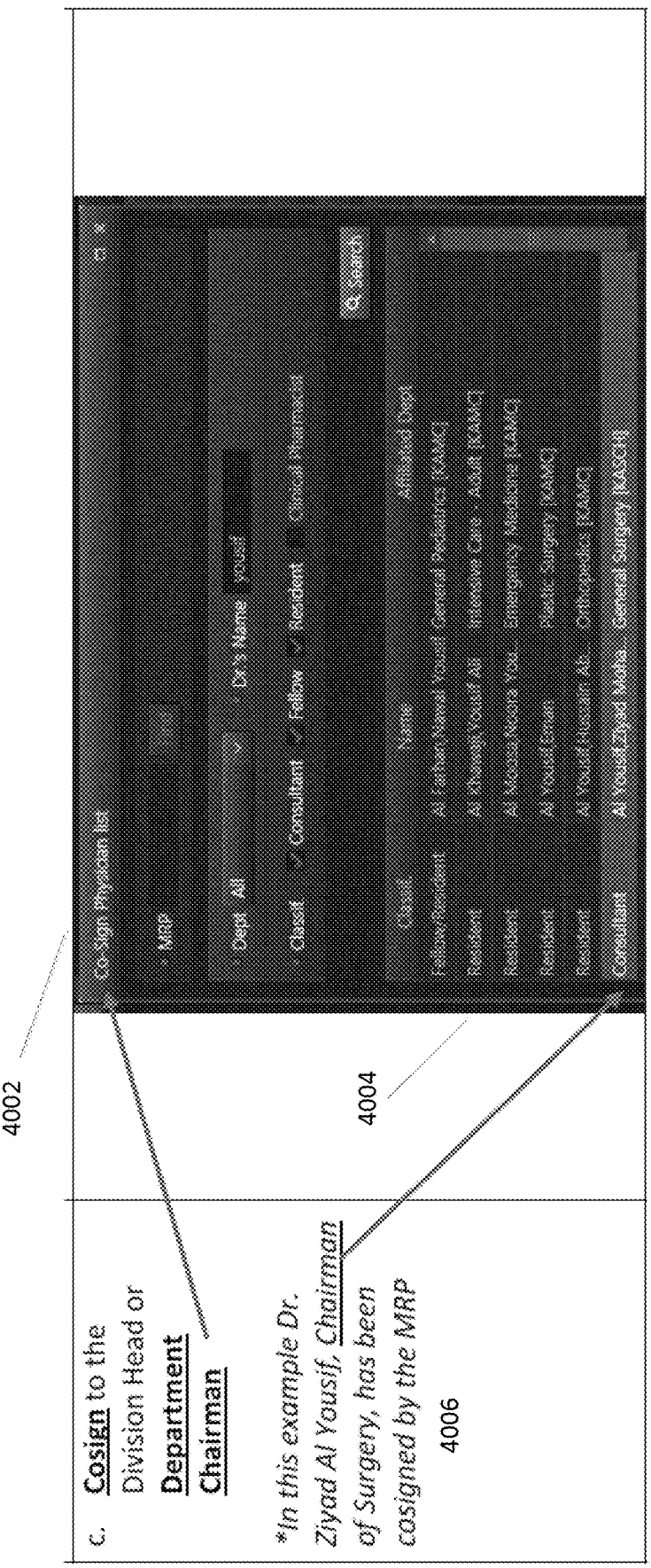
FIG. 40 illustrates a portion of a screen that may be displayed to a responsible physician in order to request a department chairmen to cosign.

FIG. 40 illustrates a portion 4002 of a screen that may be displayed to a responsible physician in order to request a department chairmen to cosign. In the example, a department chairmen 4006 is selected from a list of physicians 4004 that may serve as a cosign for the responsible physician. In S762, the department chairmen will be notified by e-mail message, telephone call, text message and/or pager that their assistance is being requested in order to resolve risk assessment issues that need to be resolved.

FIG. 41 illustrates a portion 4102 of a screen that may be displayed to the recipient of the cosign request. The recipient may be subject to a time constraint, which may be set based on the scanning process of FIG. 10. In S764, the screen display may show a list of checkboxes for actions that can be taken to resolve risk assessment issues. In S766, resolution of issues should be performed by a time T2. If risk assessment issues remain unresolved by the time T2, in S768, an escalation process will automatically be initiated. At this point, actions that have been taken in S764 may be sufficient to resolve all risk assessment issues and the escalation process ends. In S770, a screen display may show a list of checkboxes for actions that can be taken to resolve risk assessment issues. Again, actions that have been taken in S770 may be sufficient to resolve all risk assessment issues and the escalation process ends.

Referring back to FIG. 41, the recipient department chairmen may select 4104 actions (select checkboxes) that they have taken to resolve the patient's identified risk issues.

FIG. 42 illustrates a further escalation process that may occur when the department chairmen could not resolve identified risk issues in S770. In one embodiment, a further escalation process may be made to assign, in S774, the unresolved risk assessment issues, S772, to CCPID. The further escalation process 4202 may be initiated by selection 4204 of an action that indicates that issues remain unresolved and should be escalated to CCPID. An e-mail message may be sent to CCPID requesting that actions require assistance to be resolved. In S776, CCPID may communicate with the department chairmen, regional medical services, or chairmen to resolve remaining risk assessment issues within the remaining time. CCPID may be selected to request a cosign 4206. All actions taken to resolve remaining risk assessment issues may be documented for the patient.

Numerous modifications and variations of the present invention are possible in light of the above teachings. It is therefore to be understood that within the scope of the appended claims, the invention may be practiced otherwise than as specifically described herein.

The invention claimed is:

1. A method for risk scoring and inpatient care coordination, comprising:
    collecting risk criteria for a patient during inpatient care with a hybrid electronic ID/key system connected to a computer system;
    assessing one or more of the risk criteria for poorly coordinated care for the patient during the inpatient care by a first medical practitioner,
    classifying a risk assessment of the poorly coordinated care based on the assessed criteria, wherein the risk assessment has a qualitative value of no risk, medium risk, and a high risk, wherein a risk assessment of medium risk is subject to resolution locally, while patients that have a risk assessment of high risk require escalation,
    wherein the collecting, assessing and classifying are carried out with the hybrid electronic ID/key system connected to the computer system; wherein the hybrid electronic ID/key system further includes and the computer system is further connected to:
    a transmitter device having circuitry for storing ID data for the patient and transmitting a signal containing the ID data, and
    a key having a predetermined shape on a surface of the hybrid electronic ID/key;
    a radio frequency receptor device having circuitry, storing location information, for detecting the signal containing ID data, a matching detection section configured to match the predetermined shape of the key, and a movement tracking portion to track movement of the predetermined shape as the key is rotated; and
    wherein the computer system includes a patient database, configured to
    receive the ID data in conjunction with the location information from the radio frequency receptor device when the predetermined shape is completely rotated to a final position, and
    store the ID data, location information, together with patient data associated with the location.

2. The method of claim 1,
    wherein the radio frequency receptor is configured to transmit a beginning time to mark beginning of care for the inpatient care for the patient when the protruding predetermined shape is completely rotated to a position in which the notched portion comes into contact with an end of the cavity and creates a link between the ID data and the patient's electronic medical record,
    wherein the computer system utilizes the link to electronically record resolved medical issues together with the ID data, and
    wherein when at least one medical issue remains unresolved by the end of a time period based on the transmitted beginning time, an escalation process is initiated by the computer system.

3. The method of claim 1, further comprising:
    at least one nursing station device in communication with the computer system, the computer system further configured to
    extract medical history information for the patient from the patient electronic medical record during the inpatient care,
    the at least one nursing station device configured to
    display the extracted medical history information, and
    assess one or more of the criteria for poorly coordinated care for the patient during the inpatient care by the first medical practitioner,
    when the risk assessment is high risk, determine an escalation process to be performed as a plurality of predetermined time periods based on the assessed criteria in order to escalate coordination of inpatient care to care performed by at least one second medical practitioner and to resolve medical issues related to the criteria for unresolved issues during care by the first medical practitioner within a first predetermined time period, in which the predetermined time periods are conditioned based on resolution of the medical issues,
    assess actions taken by the second medical practitioner to resolve the unresolved medical issues related to the criteria for the poorly coordinated care within the conditional time periods, thereby improving timely quality of care of the patient, and
    record in the database of the computer system, the assessed criteria, the risk assessment, the determined escalation process, and the actions taken in order to relate the determined escalation process to the assessed criteria.

4. The method of claim 3, wherein the nursing station device is further configured to display the one or more criteria as a checkbox list that includes one or more of
    the patient is not in an appropriate department for current clinical needs,
    the patient is not being evaluated by an appropriate MRP for the current clinical needs,
    the patient requires one or more consultations,
    the patient has not been physically checked by a consultant for more than 24 hours of a request for consultation,
    a follow up physical check has not been performed for more than 48 hours, and
    the patient has had their procedure cancelled or delayed due to non-clinical reason.

5. The method of claim 3, wherein the one or more criteria that require a quantitative value include one or more of the patient requires one or more consultations, the patient had a procedure cancelled or delayed due to non-clinical reason, and wherein the nursing station device is further configured to expand the displayed quantitative value criteria to a number of sub-criteria to accommodate the quantitative value.

6. The method of claim 5, wherein the computer system is further configured to adjust the risk assessment based on a change in the quantitative value.

7. The method of claim 3, wherein the computer system is further configured to dynamically train a recommender system model based on the recorded assessed criteria, a risk identified, the actions taken and the escalation process.

8. The method of claim 7, wherein the recommender system model provides actions to resolve the medical issues related to the criteria for unresolved issues during care by the first medical practitioner within the first predetermined time period.

9. The method of claim 3, wherein when the actions that are taken fail to resolve at least one criteria for poorly coordinated care within the predetermined time periods, the computer system is configured to perform a further escalation process to escalate coordination of inpatient care to at least one next medical practitioner.

\* \* \* \* \*